US010898608B2

(12) United States Patent
Johnson et al.

(10) Patent No.: US 10,898,608 B2
(45) Date of Patent: Jan. 26, 2021

(54) METHODS OF IMPROVING BONE-SOFT TISSUE HEALING USING ELECTROSPUN FIBERS

(71) Applicant: NANOFIBER SOLUTIONS, LLC, Hilliard, OH (US)

(72) Inventors: Jed Johnson, London, OH (US); Jason Chakroff, Columbus, OH (US); Devan Ohst, Columbus, OH (US); Brian Cohen, Dublin, OH (US); Anthony Romeo, Chicago, IL (US)

(73) Assignee: NANOFIBER SOLUTIONS, LLC, Hilliard, OH (US)

( * ) Notice: Subject to any disclaimer, the term of this patent is extended or adjusted under 35 U.S.C. 154(b) by 0 days.

(21) Appl. No.: 15/887,301

(22) Filed: Feb. 2, 2018

(65) Prior Publication Data
US 2018/0221537 A1    Aug. 9, 2018

Related U.S. Application Data

(60) Provisional application No. 62/453,737, filed on Feb. 2, 2017, provisional application No. 62/583,530, filed
(Continued)

(51) Int. Cl.
*A61L 27/18*      (2006.01)
*A61L 27/12*      (2006.01)
(Continued)

(52) U.S. Cl.
CPC .......... *A61L 27/18* (2013.01); *A61B 17/0401* (2013.01); *A61L 27/10* (2013.01);
(Continued)

(58) Field of Classification Search
CPC .......... A61L 27/10; A61L 27/12; A61L 27/18; A61L 27/3662; A61L 27/46;
(Continued)

(56) References Cited

U.S. PATENT DOCUMENTS

| 4,738,740 A | 4/1988 | Pinchuk et al. |
| 5,258,027 A | 11/1993 | Berghaus |
| (Continued) |

FOREIGN PATENT DOCUMENTS

| AU | 2009207489 82 | 9/2014 |
| CN | 102008755 A | 4/2011 |
| (Continued) |

OTHER PUBLICATIONS

Baker et al. "The Potential to Improve Cell Infiltration in Composite Fiber-Aligned Electrospun Scaffolds by the Selective Removal of Sacrificial Fibers", Biomaterials, May 2008, pp. 2348-2358, vol. 29, Issue 15, Elsevier. DOI: 10.1016/j.biomaterials.2008.01.032.
(Continued)

*Primary Examiner* — George J Ulsh
(74) *Attorney, Agent, or Firm* — Troutman Pepper Hamilton Sanders LLP

(57) ABSTRACT

The instant disclosure is directed to methods of improving bone-soft tissue healing using biocompatible electrospun polymer fibers. In one embodiment, a method may include locating a portion of a subject's bone, affixing a tendon or ligament to the bone using a hardware fixture, and placing a patch comprising at least one electrospun polymer fiber in physical communication with both the bone and the tendon or ligament. In some embodiments, the bone may be a humerus, and the tendon or ligament may be a supraspinatus tendon. In certain embodiments, the patch may comprise substantially parallel electrospun polymer fibers, and may be placed such that the fibers are also substantially parallel with the long axis of the tendon or ligament.

16 Claims, 12 Drawing Sheets

Related U.S. Application Data on Nov. 9, 2017, provisional application No. 62/596,179, filed on Dec. 8, 2017.

(51) Int. Cl.

| | |
|---|---|
| *A61L 27/10* | (2006.01) |
| *A61L 27/36* | (2006.01) |
| *A61B 17/04* | (2006.01) |
| *A61L 27/46* | (2006.01) |
| *A61F 2/08* | (2006.01) |
| *A61B 17/00* | (2006.01) |

(52) U.S. Cl.
CPC ............ *A61L 27/12* (2013.01); *A61L 27/3662* (2013.01); *A61L 27/46* (2013.01); *A61B 2017/00526* (2013.01); *A61B 2017/00884* (2013.01); *A61B 2017/0406* (2013.01); *A61B 2017/0414* (2013.01); *A61B 2017/0464* (2013.01); *A61B 2017/0495* (2013.01); *A61F 2/0811* (2013.01); *A61F 2002/0852* (2013.01); *A61F 2002/0858* (2013.01); *A61L 2300/64* (2013.01); *A61L 2430/10* (2013.01)

(58) Field of Classification Search
CPC ............. A61L 2300/64; A61L 2430/10; A61B 2017/00526; A61B 2017/00884; A61B 2017/0406; A61B 2017/0414; A61B 2017/0464; A61B 2017/0495; A61B 17/0401; A61F 2/0811; A61F 2002/0858

See application file for complete search history.

(56) References Cited

U.S. PATENT DOCUMENTS

| | | | |
|---|---|---|---|
| 5,628,788 A | 5/1997 | Pinchuk | |
| 6,143,022 A | 11/2000 | Shull et al. | |
| 6,592,623 B1 | 7/2003 | Bowlin et al. | |
| 7,115,220 B2 | 10/2006 | Dubson et al. | |
| 7,172,765 B2 | 2/2007 | Chu et al. | |
| 7,220,281 B2 | 5/2007 | Lambrecht et al. | |
| 7,390,760 B1 | 6/2008 | Chen et al. | |
| 7,490,563 B2 | 2/2009 | Eastin et al. | |
| 7,629,030 B2 | 12/2009 | Robertson et al. | |
| 7,718,351 B2 | 5/2010 | Ying et al. | |
| 7,993,567 B2 | 8/2011 | Scott-Cannell et al. | |
| 8,157,722 B2 | 4/2012 | Arnal et al. | |
| 8,728,463 B2 | 5/2014 | Atala et al. | |
| 9,334,476 B2 | 5/2016 | Arinzeh et al. | |
| 9,737,632 B2 | 8/2017 | Johnson et al. | |
| 9,771,557 B2 | 9/2017 | Arinzeh et al. | |
| 10,562,225 B2 | 2/2020 | Johnson | |
| 2002/0022862 A1 | 2/2002 | Grafton et al. | |
| 2002/0090725 A1 | 7/2002 | Simpson et al. | |
| 2002/0142458 A1 | 10/2002 | Williams et al. | |
| 2003/0168756 A1 | 9/2003 | Balkus, Jr. et al. | |
| 2003/0211130 A1 | 11/2003 | Sanders et al. | |
| 2003/0226750 A1 | 12/2003 | Fenn | |
| 2004/0037813 A1 | 2/2004 | Simpson et al. | |
| 2005/0177249 A1 | 8/2005 | Kladakis et al. | |
| 2005/0220848 A1 | 10/2005 | Bates | |
| 2005/0277985 A1 | 12/2005 | Wert et al. | |
| 2006/0060999 A1 | 3/2006 | Amagasa et al. | |
| 2006/0085063 A1 | 4/2006 | Shastri et al. | |
| 2006/0128012 A1 | 6/2006 | Arinzeh et al. | |
| 2006/0134157 A1 | 6/2006 | Lehman et al. | |
| 2006/0135020 A1 | 6/2006 | Weinberg et al. | |
| 2006/0154063 A1 | 7/2006 | Fujihara et al. | |
| 2006/0204539 A1 | 9/2006 | Atala et al. | |
| 2007/0142907 A1 | 6/2007 | Moaddeb et al. | |
| 2007/0191956 A1 | 8/2007 | Prewett et al. | |
| 2007/0218118 A1 | 9/2007 | Michal et al. | |
| 2007/0232169 A1 | 10/2007 | Strickler et al. | |
| 2007/0269481 A1 | 11/2007 | Li et al. | |
| 2007/0286880 A1 | 12/2007 | Vasiliev et al. | |
| 2007/0288023 A1 | 12/2007 | Pellegrino et al. | |
| 2008/0027470 A1 | 1/2008 | Hart et al. | |
| 2008/0208323 A1 | 8/2008 | El-Kurdi et al. | |
| 2008/0208358 A1 | 8/2008 | Bellamkonda et al. | |
| 2009/0018643 A1 | 1/2009 | Hashi et al. | |
| 2009/0108503 A1 | 4/2009 | Scott-Carnell et al. | |
| 2009/0143855 A1 | 6/2009 | Weber et al. | |
| 2009/0152773 A1 | 6/2009 | Barinov et al. | |
| 2009/0162468 A1 | 6/2009 | Barinov et al. | |
| 2009/0208577 A1 | 8/2009 | Xu et al. | |
| 2009/0253328 A1 | 10/2009 | Watanabe et al. | |
| 2010/0036492 A1 | 2/2010 | Hung et al. | |
| 2010/0082114 A1 | 4/2010 | Gingras et al. | |
| 2010/0105799 A1 | 4/2010 | Rudd et al. | |
| 2010/0166854 A1 | 7/2010 | Michniak-Kohn et al. | |
| 2010/0222771 A1 | 9/2010 | Mitchell et al. | |
| 2010/0233115 A1 | 9/2010 | Patel et al. | |
| 2010/0273258 A1 | 10/2010 | Lannutti et al. | |
| 2010/0279112 A1 | 11/2010 | Kaplan et al. | |
| 2010/0303881 A1 | 12/2010 | Hoke et al. | |
| 2011/0004221 A1* | 1/2011 | Euteneuer | A61B 17/0642 606/99 |
| 2011/0022149 A1 | 1/2011 | Cox et al. | |
| 2011/0028834 A1 | 2/2011 | Zussman | |
| 2011/0030885 A1 | 2/2011 | Anneaux et al. | |
| 2011/0070283 A1 | 3/2011 | Hossainy et al. | |
| 2011/0083987 A1 | 4/2011 | Rolland et al. | |
| 2011/0098826 A1 | 4/2011 | Mauck et al. | |
| 2011/0166647 A1 | 7/2011 | Hashi et al. | |
| 2011/0177395 A1 | 7/2011 | Kamisasa | |
| 2011/0224702 A1 | 9/2011 | Van Kampen et al. | |
| 2011/0270412 A1 | 11/2011 | Bellan et al. | |
| 2012/0068384 A1 | 3/2012 | Phaneuf et al. | |
| 2012/0093717 A1 | 4/2012 | Mauck et al. | |
| 2013/0052254 A1 | 2/2013 | Arinzeh et al. | |
| 2013/0066438 A1 | 3/2013 | Seifalian | |
| 2013/0095165 A1 | 4/2013 | Olson et al. | |
| 2013/0103079 A1 | 4/2013 | Lau et al. | |
| 2013/0150963 A1 | 6/2013 | Johnson | |
| 2013/0172997 A1 | 7/2013 | Euteneuer et al. | |
| 2013/0245784 A1 | 9/2013 | Tan et al. | |
| 2013/0310920 A1 | 11/2013 | Su | |
| 2013/0338791 A1 | 12/2013 | McCullen et al. | |
| 2014/0030315 A1 | 1/2014 | Johnson et al. | |
| 2014/0057346 A1 | 2/2014 | Johnson | |
| 2014/0072951 A1 | 3/2014 | Johnson | |
| 2014/0079759 A1 | 3/2014 | Patel et al. | |
| 2014/0107700 A1 | 4/2014 | Baird et al. | |
| 2014/0107803 A1 | 4/2014 | Grosse | |
| 2014/0142718 A1 | 5/2014 | Seyedin et al. | |
| 2014/0272225 A1 | 9/2014 | Johnson | |
| 2014/0309726 A1 | 10/2014 | Wang | |
| 2015/0010607 A1 | 1/2015 | Francis et al. | |
| 2015/0110846 A1 | 4/2015 | Yu et al. | |
| 2016/0022873 A1 | 1/2016 | Besner et al. | |
| 2016/0024690 A1 | 1/2016 | Francis et al. | |
| 2016/0030640 A1 | 2/2016 | Schroeder et al. | |
| 2016/0143745 A1 | 5/2016 | Kandel et al. | |
| 2016/0317706 A1 | 11/2016 | Johnson | |
| 2016/0325015 A1 | 11/2016 | Johnson et al. | |
| 2017/0007741 A1 | 1/2017 | D'Lima et al. | |
| 2017/0182206 A1 | 6/2017 | Johnson et al. | |
| 2017/0306295 A1 | 10/2017 | Hazot et al. | |
| 2017/0319742 A1 | 11/2017 | Johnson et al. | |
| 2019/0249127 A1 | 8/2019 | Johnson | |

FOREIGN PATENT DOCUMENTS

| | | |
|---|---|---|
| CN | 102908677 A | 2/2013 |
| EP | 0416846 A2 | 3/1991 |
| EP | 0242203 A0 | 10/2010 |
| JP | 20115009786 A | 3/2011 |
| JP | 2012505320 A | 3/2012 |
| JP | 2012527217 A | 11/2012 |
| JP | 2013031595 A | 2/2013 |
| WO | 20000010622 A1 | 3/2000 |
| WO | 2010015754 A1 | 3/2001 |
| WO | 2005012606 A2 | 2/2005 |

(56) References Cited

FOREIGN PATENT DOCUMENTS

| | | |
|---|---|---|
| WO | 2006138552 A2 | 12/2006 |
| WO | 2006137659 A1 | 11/2008 |
| WO | 2009042829 A1 | 4/2009 |
| WO | 2009089035 A1 | 7/2009 |
| WO | 2010040129 A3 | 4/2010 |
| WO | 2010048281 A1 | 4/2010 |
| WO | 2010124207 A1 | 10/2010 |
| WO | 2012145739 A1 | 10/2012 |
| WO | 2013078051 A1 | 5/2013 |
| WO | 2013106822 A1 | 7/2013 |
| WO | 2014031721 A1 | 2/2014 |
| WO | 2014145864 A1 | 9/2014 |
| WO | 2015153011 A1 | 10/2015 |

OTHER PUBLICATIONS

Teo et al. "Electrospun fibre bundle made of aligned nanofibers over two fixed points" (1978) Nanotechnology 16:1878-1884.
Thomas et al. "Effects of gossypol on the cell cycle phases in T-47D human breast cancer cells" (Jul.-Aug. 1991) Anticancer Research 11(4):1469-1476 (Abstract only).
Tomlinson et al. "Loss of heterozygosity analysis: Practically and conceptually flawed?" (2002) Genes Chromosomes & Cancer 34:349-353.
Tonn et al. "Mechanisms of glioma cell invasion" (2003) Acta Neurochir Suppl 88: 163-167.
Toole "Hyaluronan and its binding proteins, the hyaladherins" (1990) Curr. Opin. Cell Biol. 2:839-844.
Tse, et al. "Current Status of Pipeline Embolization Device in the Treatment of Intracranial Aneurysms: A review" (Dec. 2013) World Neurosurgery 80(6): 829-835.
Tuszynski et al. "Differential cytotoxic effect of gossypol on human melanoma, colon carcinoma, and other tissue culture cell lines" (Feb. 1984) Cancer Research 44(2):768-771.
Van Meter et al. "The role of matrix metalloproteinase genes in glioma invasion: co-dependent and interactive proteolysis" (2001) Journal of Neuro-Oncology 53:213-235.
Zhang et al. "Recent development of polymer nanofibers for biomedical and biotechnological applications" (2005) Journal of Materials Science—Materials in Medicine 16(10):933-946.
Viapiano et al. "BEHAB/brevican requires ADAMTS—mediated proteolytic cleavage to promote glioma invasion" (2008) J. Neurooncol. 88:261-272.
Viapiano et al. "From barriers to bridges: chondroitin sulfate proteoglycans in neuropathology" (Oct. 2006) Trends Mol. Med. 12(10):488-496.
Vuorinen et al. "Debulking or biopsy of malignant glioma in elderly people—a randomized study" (2003) Acta Neurochir. 145:5-10.
Wang et al. "Conjugated Linoleic Acid (CLA) Up-regulates the Estrogen-regulated Cancer Suppressor Gene, Protein Tyrosine Phosphatase γ (PTPγ), in Human Breast Cells" (2006) Anticancer Research 26(1A):27-34.
Wang et al. "Effect of gossypol on DNA synthesis and cell cycle progression of mammalian cells in vitro" (Jan. 1984) Cancer Research 44(1):35-38.
Wang et al. "Nanofibres and their influence on Cells for Tissue Regeneration" (2005) Aust. J. Chem. 58(10):704-712.
Wang et al. "Increased Circulating Fibrocytes in Asthma with Chronic Airflow Obstruction" (2008) Am. J. Respir. Crit. Care Med. 178(6): p. 583-591.
Williams et al. "Anti-glioma effects of protein kinase inhibitors that simultaneously block invasion and proliferation" (Oct. 2007) Abstracts from 12th Annual Meeting of the Society for Neuro-Oncology 9: 486 ET-18 (Abstract only).
Wu et al. "Versican protects cells from oxidative stress-induced apoptosis" (Feb. 2005) Matrix Biology 24(1):3-13.
Wu et al. "An in vitro and in vivo study of antitumor effects of gossypol on human SW-13 adrenocortical carcinoma" (1986) Cancer Research 49(14):3754-3758.

Wykosky et al. "Soluble monomeric EphrinA1 is released from tumor cells and is a functional ligand for the EphA2 receptor" (2008) Oncogene 27(58):7260-7273.
Xie et al. "Encapsulation of protein drugs in biodegradable microparticles by co-axial electrospray" Jan. 15, 2008) Journal of Colloid and Interface Science 317(2):469-476.
Xie et al. "White matter inhibitors in CNS axon regeneration failure" (Feb. 2007) Exp. Neurol. 209(2):302-312.
Yamaguchi "Lecticans: organizers of the brain extracellular matrix" (2000) Cell Mol. Life Sci. 57:276-289.
Yang et al. "Integrin α1β1 and α2β1are the key regulators of hepatocarcinoma cell invasion across the fibrotic matrix microenvironment" (Dec. 1, 2003) Cancer Research 63(23): 8312-8317.
Yoo et al. "Surface-Functionalized Electrospun Nanofibers for Tissue Engineering and Drug Delivery" Jan. 1, 2009, Advanced Drug Delivery Reviews 61:1033-1042.
Yoshimoto et al. "A biodegradable nanofiber scaffold by electrospinning and its potential for bone tissue engineering" (May 2003) Biomaterials 24(12):2077-2082.
Yu et al. "Production of submicrometer diameter fibers by two-fluid electrospinning" (Sep. 2004) Adv. Mater. 16(17):1562-1566.
Zborowski et al. "Red blood cell magnetophoresis" (Apr. 2003) Biophysical Journal 84:2638-2645.
Zeng et al. "Enzymatic degradation of poly(L-lactide) and poly(ε-caprolactone) electrospun fibers" (Dec. 15, 2004) Macromolecular Bioscience 4(12):1118-1125.
Zeng et al. "Ultrafine fibers electrospun from biodegradable polymers" (Jul. 25, 2003) Journal of Applied Polymer Science 89(4):1085-1092.
Zhang et al. "Electrospinning of gelatin fibers and gelatin/PCL composite fibrous scaffolds" (2005) J. Biomed. Mater. Res. Part B: Appl. Biomater. 72B(1):156-165.
Barnhart et al. "Evaluation of an intra-articular synthetic ligament for treatment of cranial cruciate ligament diseaase in dogs: a six-month prospective clinical trial" Jun. 2016, Vet Comp Orthop. Traumatol. 29:491-498.
International Search Report and Written Opinion for PCT/US2018/016638 dated Apr. 23, 2018.
Aboitiz et al. "Fiber composition of the human corpus callosum" (Dec. 11, 1992) Brain Res. 598(1-2):143-153.
Albertini et al. "The effect of glycosaminoglycans and proteoglycans on lipid peroxidation" (Aug. 2000) Int. J. Mol. Med. 6(2):129-136 (Abstract only).
Alexis et al. "In Vivo Particle Uptake by Airway Macrophages in Healthy Volunteers" (2006) Am. J. Respir. Cell Mol. Biol. 34(3):305-313.
Ayres et al. "Microvascular Endothelial Cell Migration in Scaffolds of Electrospun Collagen" (Mar. 2005) Wound Repair and Regeneration 13(2):A6 (abstract only).
Band et al. "Antiproliferative effect of gossypol and its optical isomers on human reproductive cancer cell lines" (Mar. 1989) Gynecologic Oncology 32(3):273-277.
Bandtlow et al. "Proteoglycans in the developing brain: new conceptual insights for old proteins" (Oct. 2000) Physiol. Rev. 80(4):1267-1290.
Baran et al. "Important roles for macrophage colony-stimulating factor, CC chemokine ligand 2, and mononuclear phagocytes in the pathogenesis of pulmonary fibrosis" (2007) Am. J. Respir. Crit. Care Med. 176(1):78-89.
Bellail et al. "Microregional extracellular matrix heterogeneity in brain modulates glioma cell invasion" (Jun. 2004) Int. J. Biochem. Cell Biol. 36(6):1046-1069.
Beningo et al. "Nascent Focal Adhesions Are Responsible for the Generation of Strong Propulsive Forces in Migrating Fibroblasts" (May 14, 2001) J. Cell Biol. 153(4):881-887.
Benz et al. "Biochemical Correlates of the Antitumor and Antimitochondrial Properties of Gossypol Enantiomers" (Jun. 1990) Mol. Pharma. 37(6):840-847.
Benz et al. "Lactic Dehydrogenase Isozymes, 31P Magnetic-Resonance Spectroscopy, and In Vitro Antimitochondrial Tumor Toxicity With Gossypol and Rhodamine-123" (Feb. 1987) J. Clin. Invest. 79(2):517-523.

(56) References Cited

OTHER PUBLICATIONS

Benz et al. "Selective toxicity of gossypol against epithelial tumors and its detection by magnetic resonance spectroscopy" (Mar. 1988) Contraception 37(3):221-228.
Bernstein et al. "Glioblastoma cells do not intravasate into blood vessels" (Jan. 1995) Neurosurgery 36(1):124-132.
Bershadsky et al. "Adhesion-mediated mechanosensitivity: a time to experiment, and a time to theorize" (Oct. 2006) Curr. Opn. Cell Biol. 18(5):472-481.
Binder et al. "Proteases and the Biology of Glioma Invasion" (2002) J. Neuro-Oncology 56:149-158.
Bucala et al. "Circulating Fibrocytes Define A New Leukocyte Subpopulation That Mediates Tissue Repair" (Nov. 1994) Mol. Med. 1(1):71-81.
Gladson "The Extracellular Matrix of Gliomas: Modulation of Cell Function" (Oct. 1999) J. Neuropath. Exper. Neur. 58(10):1029-1040.
Camoretti-Mercado "Targeting the airway smooth muscle for asthma treatment" (Oct. 2009) Translational Research 154(4):165-174.
Cattaruzza et al. "Proteoglycan control of cell movement during wound healing and cancer spreading" (Sep. 2005) Matrix Biol. 24(6):400-417.
Central Brain Tumor Registry of the United States, Primary Brain Tumors in the United States—Statistical Report 1998-2002, CBTRUS 2005-2006.
Chalmers et al. "Chapter 9, Preparative applications of magnetic separation in biology and medicine" (2007) Laboratory Techniques in Biochemistry and Molecular Biology 32:249-264 (Abstract only).
Chen et al., Preparation and Characterization of Coaxial Electrospun Thermoplastic Polyurethane/Collagen Compound Nanofibers for Tissue Engineering Applications, Colloids and Surfaces B-Biointerfaces (2010), 79(2):315-325.
Chew et al. "The Role of Electrospinning in the Emerging Field of Nanomedicine" 2006, Curr. Pharm. Sec. 12(36) A:4751-4770.
Chicoine et al. "Assessment of brain-tumor cell motility in vivo and in vitro" (Apr. 1995) J. Neurosurg. 82(4):615-622.
Choi et al. "Structuring electrospun polycaprolactone nanofiber tissue scaffolds by femtosecond laser ablation" (Nov. 2007) J. Laser Appl. 19(4):225-231.
Cukierman et al. "Taking cell-matrix adhesions to the third dimension" (Nov. 23, 2001) Science 294:1706-1712.
Davies et al. "Adult axon regeneration in adult CNS white matter" (Dec. 1, 1998) Trends Neurosci. 21(12):515.
Delpech et al. "Hyaluronan and hyaluronectin in the nervous system" (Sep. 28, 2007) Ciba Foundation Symposium 143—The Biology of Hyaluronan (Abstract only).
Diaz et al. "Controlled encapsulation of hydrophobic liquids in hydrophilic polymer nanofibers by co-electrospinning" (2006) Adv. Funct. Mater. 16(16):2110-2116.
Discher et al. "Tissue cells feel and respond to the stiffness of their substrate" (Nov. 18, 2005) Science 310:1139-1143.
Drilling et al. "Fabrication of burst pressure competent vascular grafts via electrospinning: Effects of microstructure" (Mar. 15, 2009) J. Miomed. Mat. Res. Part A 88A(4):923-934.
Duling et al. "Mechanical characterization of electrospun Polycaprolactone (PCL): a potential scaffold for tissue engineering" (Feb. 2008) J. Biomech. Eng. 130(1) No. 011006.
Engler et al. "Matrix Elasticity Directs Stem Cell Lineage Specification" (Aug. 25, 2006) Cell 126(4):677-689.
Epperly et al. "Correlation of Ionizing Irradiation-induced Late Pulmonary Fibrosis with Long-term Bone Marrow Culture Fibroblast Progenitor Cell Biology in Mice Homozygous Deletion Recombinant Negative for Endothelial Cell Adhesion Molecules" (2004) In Vivo 18(1):1-14.
Erbel et al., "Aortic Dimensions and the Risk of Dissection," Heart (Jan. 2006), 92(1) pp. 137-142.
Farin et al. "Transplanted glioma cells migrate and proliferate on host brain vasculature: a dynamic analysis" (Jun. 2006) Glia 53(8):799-808.
Fathallah-Shaykh "Darts in the Dark Cure Animal, but Not Human, Brain Tumors" (May 2002) Arch. Neurol. 59:721-724.
Frey et al. "Eiectrospinning and Porosity Measurements of Nylon6 PEO blended Nonwovens" Journal of Engineered Fibers and Fabrics (2007) 2(1):31-37.
Fujihara et al"Guided bone regeneration membrane made of Polycaprolactone/calcium carbonate composite nano-fibers" (Jul. 2005) Biomaterials 26(19):4139-4147.
Furnari et al. "Malignant astrocytic glioma: genetics, biology, and paths to treatment" (2007) Genes Dev. 21:2683-2710.
Gaumer et al. "Structure-function relationships and Source-to-ground Distance and the Mechanical Properties of Electrospun Fiber" Acta Biomaterialia 5(5):1552-1561.
Geiser et al. "The Role of Macrophages in the Clearance of Inhaled Ultrafine Titanium Dioxide Particles" (2008) Am. J. Respir. Cell Mol. Biol. 38(3):371-376.
Georges et al. "Cell type-specific response to growth on soft materials" (Apr. 2005) J. Appl. Physiol. 98:1547-1553.
Georges et al. "Matrices with compliance comparable to that of brain tissue select neuronal over glial growth in mixed cortical cultures" (Apr. 2006) Biophys. J. 90:3012-3018.
Giese et al. "Dichotomy of astrocytoma migration and proliferation" (1996) Int. J. Cancer 67:275-282.
Giese et al. "Glioma cell adhesion and migration on human brain sections" (1998) Anticancer Res. 18(4A):2435-2447 (Abstract only).
Giese et al. "Migration of Human Glioma Cells on Myelin" (Apr. 1996) Neurosurgery 38(4):755-764.
Giese et al. "Substrates for astrocytoma invasion" (Aug. 1995) Neurosurgery 37(2):294-302.
Gilbert et al. "Antiproliferative activity of gossypol and gossypolone on human breast cancer cells" (May 26, 1995) Life Sciences 57(1):61-67.
Lo et al. "Cell movement is guided by the rigidity of the substrate" (Jul. 2000) Biophysical Journal 79(1);144-152.
Luu et al. "Development of a nanostructured DNA delivery scaffold via electrospinning of PLGA and PLGA and PLA-PEG block copolymers" (Apr. 29, 2003) Journal of Controlled Release 89(2):341-353.
Macchiarini et al. "Clinical Transplantation of a Tissue-Engineered Airway" (Dec. 13, 2008) The Lancet 372 (9655):2023-2030.
Martins et al. "Electrospun nanostructured scaffolds for tissue engineering applications" (2007) Nanomedical 2(6):929-942.
Mathews "Preparation and anisotropic mechanical behavior of highly-oriented electrospun poly(butylene terephthalate) fibers" Aug. 2006, Journal of Applied Polymer Science 101(3):2017-2021.
McClure et al. "A Three-Layered Electrospun Matrix to Mimic Native Arterial Architecture Using Polycaprolactone, Elastin, and Collagen: A Preliminary Study" 2010, Acta Biomaterialia 6:2422-2433.
Meng et al., Electrospun aligned nanofibers composite of MWCNT/polyurethane to enhance vascular endothelium cells proliferation and function, Journal of Nanoscience and Nanotechnology (Jul. 8, 2010) pp. 312-320.
Morawski et al. "Perineuronal nets potentially protect against oxidative stress" (Aug. 2004) Exp. Neurol. 188(2):309-315.
Morgenstern et al. "Chondroitin sulphate proteoglycans in the CNS injury response" (2002) Prog. Brain Res. 137:313-332.
Mori et al. "Fibrocytes contribute to the myofibroblast population in wounded skin and originate from the bone marrow" (Mar. 10, 2005) Experimental Cell Research 304(1):81-90.
Murray et al. "Hyper-responsiveness of IPF/UIP fibroblasts: Interplay between TGF β1, IL-13 and CCL2" (2008) 40(10):2174-2182.
Nam et al. "Improved Cellular Infiltration in Electrospun Fiber via Engineered Porosity" (Sep. 2007) Tissue Engineering 13(9):2249-2257.
Nam et al. "Materials selection and residual solvent retention in biodegradable electrospun fibers" (Feb. 5, 2008) Journal of Applied Polymer Science 107(3):1547-1554.
Nam et al. "Modulation of Embryonic Mesenchymal Progenitor Cell Differentiation via Control Over Pure Mechanical Modulus in Electrospun Nanofibers" (Apr. 2011) Acta Biomaterialia 7(4):1516-1524.

(56) References Cited

OTHER PUBLICATIONS

Nam et al. "Novel Electrospun Scaffolds for the Molecular Analysis of Chondrocytes Under Dynamic Compression" 2009. Tissue Engineering Part A 15(3):513-523.
Ninomiya et al. "Transforming Growth Factor—β Signaling Enhances Transdifferentiation of Macrophages into Smooth Muscle-Like Cells" (2006) Hypertension Research 29(4):269-276.
Norton et al. "Myelination in rat brain: method of myelin isolation" (Oct. 1973) J. Neurochem. 21(4):749-757.
Novak et al. "Extracellular matrix and the brain: components and function" (2000) J. Clin. Neurosci. 7(4):280-290.
Ohnishi et al. "A Novel Model of Glioma Cell Invasion Using Organotypic Brain Slice Culture" (Jul. 15, 1998) Cancer Res. 58:2935-2940.
Palfi et al. "Correlation of in vitro infiltration with glioma histological type in organotypic brain slices" (2004) Br. J. Cancer 91(4):745-752.
Park, "Lab-made organ implanted for first time" (Jul. 14, 2017), CNN.com <http://www.cnn.com/2011/HEALTH/07/07/trachea.transplant/index.html>.
Pelham Jr. et al. "Cell locomotion and focal adhesions are regulated by substrate flexibility" (Dec. 1997) PNAS USA 94:13661-13665.
Pham et al., Electrospinning of Polymeric Nanofibers for Tissue Engineering Applications: A Review, Tissue Engineering(2006), 12(5):1197-1211.
Pilkington "The paradox of neoplastic glial cell invasion of the brain and apparent metastatic failure" (1997) Anticancer Res. 17(6B):4103-4105 (Abstract).
Powell et al. "EDC cross-linking improves skin substitute strength and stability" (2006) Biomaterials 27(34): 5821-5827.
Properzi et al. "Proteoglycans and Brain Repair" (Feb. 2004) News Physiol. Sci. 19:33-38.
Quigley et al. "The relationship between survival and the extent of the resection in patients with supratentorial malignant gliomas" (1991) Neurosurgery 29:385-389.
Rao "Molecular mechanisms of glioma invasiveness: the role of proteases" (Jul. 2003) Nature Reviews Cancer 3:489-501.
Rath et al. "Compressive Forces Induce Osteogenic Gene Expression in Calvarial Osteoblasts" (2008) Journal of Biomechanics 41(5):1095-1103.
Rauch "Extracellular matrix components associated with remodeling processes in brain" (2004) Cell Mol. Life Sci. 61:203102045.
Reneker et al. "Nanometre diameter fibres of polymer, produced by electrospinning" (1996) Nanotechnology 7(3):216-223.
Rocks et al. "ADAMTS-1 Metalloproteinase Promotes Tumor Development through the induction of a Stromal Reaction In vivo" (2008) Cancer Research 68(22):9541-9550.
Ruoslahti "Brain extracellular matrix" (1996) Glycobioloqhy 6(5):489-492.
Samios et al., "In situ compatibilization of polyurethane with poly(ethylene terephthalate)," Department of Chemistry, European Polymer Journal (2000), 36 pp. 937-947.
Sasmono et al. "A macrophage colony-stimulating factor receptor—green fluorescent protein transgene is expressed throughout the mononuclear phagocyte system of the mouse" (2003) Blood 101(3):1155-1163.
Saunders et al. "Fibrocyte localization to the airway smooth muscle is a feature of asthma" (Feb. 2009) Journal of Allergy and Clinical Immunology 123(2): 376-384.
Schiffer et al. "Cell proliferation and invasion in malignant gliomas" (1997) Anticancer Research 17(1A):61-69 (Abstract only).
Schmidt et al. "Identification of Circulating Fibrocytes as Precursors of Bronchial Myofibroblasts in Asthma" (2003) Journal of Immunology 171(1):380-389.
Shin et al. "Contractile cardiac grafts using a novel nanofibrous mesh" (Aug. 2004) Biomaterials 25(17):3717-3723.
Shin et al. "In Vivo Bone Tissue Engineering Using Mesenchymal Stem Cells on a Novel Electrospun Nanofibrous Scaffold" (Jul. 9, 2004) Tissue Engineering 10(1-2):33-41.
Sieben et al. "PCR artifacts in LOH and MSI analysis of microdissected tumor cells" (Nov. 2000) Human Pathology 31(11):1414-1419.
Silver et al. "Regeneration beyond the glial scar" (Feb. 2004) Nature 5:146-156.
Srikar et al. "Desorption-limited mechanism of release from polymer nanofibers" (2008) Langmuir 24(3):965-974.
Stein et al. "Estimating the cell density and invasive radius of three-dimensional glioblastoma tumor spheroids grown in vitro" (Aug. 1, 2007) Applied Optics 46(22):5110-5118.
Stitzel et al. "Controlled Fabrication of a Biological Vascular Substitute" 2006, Biomaterials 27:1088-1094.
Subramanian et al. "Metastasis to and from the central nervous system—the 'relatively protected site'" (Aug. 2002) The Lancet Oncology 3(6):498-507.
Supplemental European Search Report and Written Opinion for EP15774154 dated Sep. 22, 2017.
Swanson et al. "A quantitative model for differential motility of gliomas in grey and white matter" (Oct. 2000) Cell Proliferation 33(5):317-329.
Swanson "Quantifying glioma cell growth and invasion in vitro" (2008) Mathematical and Computer Modeling 47:638-648.
Teo et al. "A review on electrospinning design and nanofibre assemblies" (2006) Nanotechnology 17(14):R89-R106.
Goldbrunner et al. "Cell-extracellular matrix interaction in glioma invasion" (1999) Acta Neurochir (Wien) 141:295-305.
Grandpre et al. "Nogo: a molecular determinant of axonal growth and regeneration" (Oct. 2001) Neuroscientist 7(5):377-386.
Haley et al. "Study of myelin purity in relation to axonal contamination" (1980) Cell Mol. Neurobiol. 1:175-187.
Hashi et al. "Antithrombogenic Modification of Small Diameter Microfibrous Vascular Grafts" Arterioscler Thromb Vasc Biol. (Aug. 2010) 30(8):1621-1627.
Hashi et al. "Antithrombogenic Property of Bone Marrow Mesenchymal Stem Cells in Nanofibrous Vascular Grafts" Jul. 17, 2007, PNAS 104(29):11915-11920.
He et al. "Fabrication of Drug-Loaded Electrospun Aligned Fibrous Threads for Suture Applications" 2009, J. Biomed. Mater. Research, Part A 89(1):80-95.
Hinz et al. "Alpha-smooth muscle actin expression upregulates fibroblast contractile activity" (Sep. 2001) Molecular Biology of the Cell 12(9):2730-2741.
Holland "Glioblastoma multiforme; the terminator" (Jun. 6, 2000) PNAS USA 97(12):6242-6244.
Hsu et al. "N,N-Dimethyiformamide Additions to the Solution for the Electrospinning of Poly(ϵ-caprolactone) Nanofibers" (Apr. 2004) Macromolecular Materials and Engineering 289(4):334-340 (Abstract only).
Hsu et al. "Nano-sized beads and porous fiber constructs of Poly(ϵ-caprolactone) produced by electrospinning" (2004) Journal of Material Science 39(9):3003-3013.
Hu et al. "Gossypol inhibits basal and estrogen-stimulated DNA synthesis in human breast carcinoma cells" (1993) Life Sciences 53(25):PL433-PL438.
Hu et al. "Regulating axon growth within the postnatal central nervous system" (Dec. 2004) Semin Perinatol 28(6):371-378.
Hu et al. "The proteoglycan brevican binds to fibronectin after proteolytic cleavage and promotes glioma cell motility" (Sep. 5, 2006) Journal of Biological Chemistry 283(36):24848-24859.
Huang et al. "A review on polymer nanofibers by electrospinning and their applications in nanocomposites" (Nov. 2003) Composites Science and Technology 63(15):2223-2253.
International Search Report and Written Opinion for PCT/US2015/016973 dated May 22, 2015.
International Search Report and Written Opinion for PCT/US2016/030058 dated Jul. 29, 2016.
International Search Report and Written Opinion for PCT/US2016/60157 dated Jan. 31, 2017.
Jaroszewski et al. "Action of Gossypol and Rhodamine 123 on Wild Type and Multidrug-resistant MCF-7 Human Breast Cancer Cells: 31P Nuclear Magnetic Resonance and Toxicity Studies" (1990) Cancer Research 50 (21):6936-6943.

(56) References Cited

OTHER PUBLICATIONS

Johnson "First-in-the-World Equine Joint Injection for Osteoarthritis" (Jul./Aug. 2014) The International Equine Veterinarian 23-25.
Johnson et al. "Electrospun PCL in Vitro: a Microstructural Basis for Mechanical Property Changes" (2009) Journal of Biomaterials Science, Polymer Edition 20(4):467-481.
Johnson et al. "Microstructure-Property Relationships in a Tissue-Engineering Scaffold" (2007) Journal of Applied Polymer Science 104(5):2919-2927.
Johnson et al. "Quantitative Analysis of Complex Glioma Cell Migration on Electrospun Polycaprolcatone Using Time-Lapse Microscopy" (2009) Tissue Engineering Part C 15(4):531-540.
Jung et al. "Tracking the invasiveness of human astrocytoma cells by using green fluorescent protein in an organotypical brain slice model" (Jan. 2001) J. Neurosurgery 94(1):80-89.
Kang et al. Plasma Treatment of Textiles—synthetic Polymer-Base Textiles (2004) AATCC Review 4(11):29-33.
Katta et al. "Continuous electrospinning of aligned polymer nanofibers onto a wire drum collector" (Sep. 28, 2004) Nano Letters 4(11):2215-2218.
Kazemnejad et al. "Biochemical and Molecular Characterization of Hepatocyte-Like Cells Derived from Human Bone Marrow Mesenchymal Stem Cells on a Novel Three-Dimensional Biocompatible Nanofibrous Scaffold" Feb. 1, 2009, J. Gastronenter. Hepatol. 24(2):278-287.
Khil et al. "Novel fabricated matrix via electrospinning for tissue engineering" (2005) Journal of Biomedical Materials Research Part B—Applied Biomaterials 72B(1):117-124.
Kim et al. "Controlled protein release from electrospun biodegradable fiber mesh composed of poly($\epsilon$-caprolactone) and poly(ethylene oxide)" (Jun. 29, 2007) International Journal of Pharmaceutics 338 (1-2):276-283.
Kim et al. "Epithelial cell $\alpha 3\beta 1$ integrin links $\beta$-catenin and Smad signaling to promote myofibroblast formation and pulmonary fibrosis" (Jan. 2009) Journal of Clinical Investigation 119(1):213-224.
Kleihues et al. "The WHO Classification of Tumors of the Nervous System" (Mar. 2002) J. Neuropathol. Exp. Neurol. 61(3):215-225.
Klim et al. "A Defined Glycosaminoglycan-Binding Substratum for Human Pluripotent Stem Cells" (2010) Nature Methods 7(23):989-996.
Ko et al. "High Percentage of False-Positive Results of Cytokeratin 19 RT-PCR in Blood: A Model for the Analysis of Illegitimate Gene Expression" (2000) Oncology 59:81-88.
Kwon et al. "Electrospun nano- to microfiber fabrics made of biodegradable copolyesters: structural characteristics, mechanical properties and cell adhesion potential" (Jun. 2005) Biomaterials 26(18):3929-3939.
Lannutti et al. "Electrospinning for tissue engineering scaffolds" (Apr. 2007) Materials Science and Engineering: C 27(3):504-509.
Leblanc et al. "An in vitro study of inhibitory activity of gossypol, a cottonseed extract, in human carcinoma cell lines" (Dec. 2002) Pharmacological Research 46(6):551-555.
Lee et al., "Biomedical Applications of Magnetically Functionaiized Organic/Inorganic Hybrid Nanofibers." International Journal of Molecular Sciences (2015), 16 pp. 13661-13677.
Lee et al. "Characterization of nano-structured poly($\epsilon$-caprolactone) nonwoven mats via electrospinning" (Feb. 2003) Polymer 44(4):1287-1294.
Lesma et al. "Glycosaminoglycans in nerve injury: I. Low doses glycosaminoglycans promote neurite formation" (Dec. 1, 1996) J. Neurosci. Res. 46(5):565-571.
Levicar et al. "Proteases in brain tumour progression" (2003) Acta Neurochir. (Wien.) 145:825-838.
Levina et al. "Chemotherapeutic drugs and human tumor cells cytokine network" (2008) International Journal of Cancer 123(9):2031-2040.
Li et al. "A three-dimensional nanofibrous scaffold for cartilage tissue engineering using human mesenchymal stem cells" (Feb. 2005) Biomaterials 26(6):599-609.
Li et al. "Biological response of chondrocytes cultured in three-dimensional nanofibrous poly($\epsilon$-caprolactone) scaffolds" (Dec. 15, 2003) Journal of Biomedical Materials Research Part A 67A(4):1105-1114.
Li et al. "Electrospinning nanofibers as uniaxially aligned arrays and layer-by-layer stacked films" (Feb. 2004) Advanced Materials 16(4):361-366.
Li et al. "Multilineage differentiation of human mesenchymal stem cells in a three-dimensional nanofibrous scaffold" (Sep. 2005) Biomaterials 26(25):5158-5166.
Liang et al. "Developing gossypol derivatives with enhanced antitumor activity" (1995) Investigational New Drugs 13(3):181-186.
Lieblein et al. "STAT3 can be activated through paracrine signaling in breast epithelial cells" (2008) BMC Cancer 8(302):1-14 :302.
Liu et al. "Function analysis of estrogenically regulated protein tyrosine phosphatase $\gamma$ (PTP$\gamma$) in human breast cancer cell line MCF-7" (2004) Oncogene 23(6):1256-1262.
Liu et al. "Involvement of breast epithelial-stromal interactions in the regulation of protein tyrosine phosphatase-$\gamma$ (PTP$\gamma$) mRNA expression by estrogenically active agents" (2002) Breast Cancer Research and Treatment 71(1):21-35.
Liu et al. The (−)—enantiomer of gossypol possesses higher anticancer potency than racemic gossypol in human breast cancer: (2002) Anticancer Research 22(1A):33-38 (Abstract only).
Liu et al. "Transformation of MCF-10A Human Breast Epithelial Cells by Zeranol and Estradiol-17beta" (Nov.-Dec. 2004) Breast J. 10(6):514-521.
International Search Report and Written Opinion for PCT/US2018/064570 dated Feb. 6, 2019.
Kim et al. "Evaluations of Chitosan/Poly(D,L-lactic-co-glycolic acid) Composite Fibrous Scaffold for Tissue Engineering Application" 2013, Macromolecular Res. 21:931-939.
Zhu et al. "Characterization of a co-electrospun scaffold of HLC/CS/PLA for vascular tissue engineering" 2014, Biio-Medical Mat. Engin. 24(6):1999-2005.
Lee et al. "Increased Mechanical Properties of Alligned and Isotropic Electrospun PVA Nanofiber Webs by Cellulose Nanowhisker Reinforcement" 2012, Macromolecular Research 20(1):76-83.
Herrera et al. "Randomly Oriented and Aligned Cellulose Fibres Reinforced with Cellulose Nanowhiskers, Prepared by Electrospinning" 2011, Plastics, Rubber and Composites 40(2):57-64.

\* cited by examiner

METHODS OF IMPROVING BONE-SOFT TISSUE HEALING USING ELECTROSPUN FIBERS

CROSS-REFERENCE TO RELATED APPLICATIONS

This application claims priority to and benefit of U.S. Provisional Application Ser. No. 62/453,737, filed Feb. 2, 2017, entitled "Methods of Improving Bone-Soft Tissue Healing Using Electrospun Fibers," U.S. Provisional Application Ser. No. 62/583,530, filed Nov. 9, 2017, entitled "Methods of Improving Bone-Soft Tissue Healing Using Electrospun Fibers," and U.S. Provisional Application Ser. No. 62/596,179, filed Dec. 8, 2017, entitled "Methods of Improving Bone-Soft Tissue Healing Using Electrospun Fibers," each of which is hereby incorporated herein by reference in its entirety.

BACKGROUND

When soft tissue, such as a tendon or ligament, tears or ruptures and pulls away from the bone to which it is attached, surgery is necessary. In a typical reconstruction surgery, such as a rotator cuff or Achilles tendon repair, a suture and suture anchor are typically used to secure the soft tissue back to the bone. Once it is "reattached" to the bone, the soft tissue and bone are expected to heal to reform a strong bone-soft tissue interface. Frequently, however, such healing is suboptimal, or is at risk for re-rupture during the healing period. Therefore, a need exists to decrease the healing time and improve the quality of the repair of the soft tissue to the bone to more closely approximate the strength and quality seen at an uninjured bone-soft tissue interface.

SUMMARY

The instant disclosure is directed to methods of improving bone-soft tissue healing using biocompatible electrospun polymer fibers. In one embodiment, a method may include locating a portion of a subject's bone, affixing a tendon or ligament to the bone using a hardware fixture, and placing a patch comprising at least one electrospun polymer fiber in physical communication with both the bone and the tendon or ligament. In some embodiments, the bone may be a humerus, and the tendon or ligament may be a supraspinatus tendon. In certain embodiments, the patch may comprise substantially parallel electrospun polymer fibers, and may be placed such that the fibers are also substantially parallel with the long axis of the tendon or ligament. In other embodiments, the patch may comprise randomly oriented electrospun polymer fibers.

In another embodiment, a method may comprise locating a humerus of a subject, affixing a supraspinatus tendon to the humerus using a hardware fixture, and placing a patch comprising at least one electrospun polymer fiber in physical communication with the humerus and the supraspinatus tendon, such that the patch is between the humerus and the supraspinatus tendon, and the suture extends through an opening in the patch. Further embodiments of the instant disclosure are described herein.

DETAILED DESCRIPTION

Figure 1:
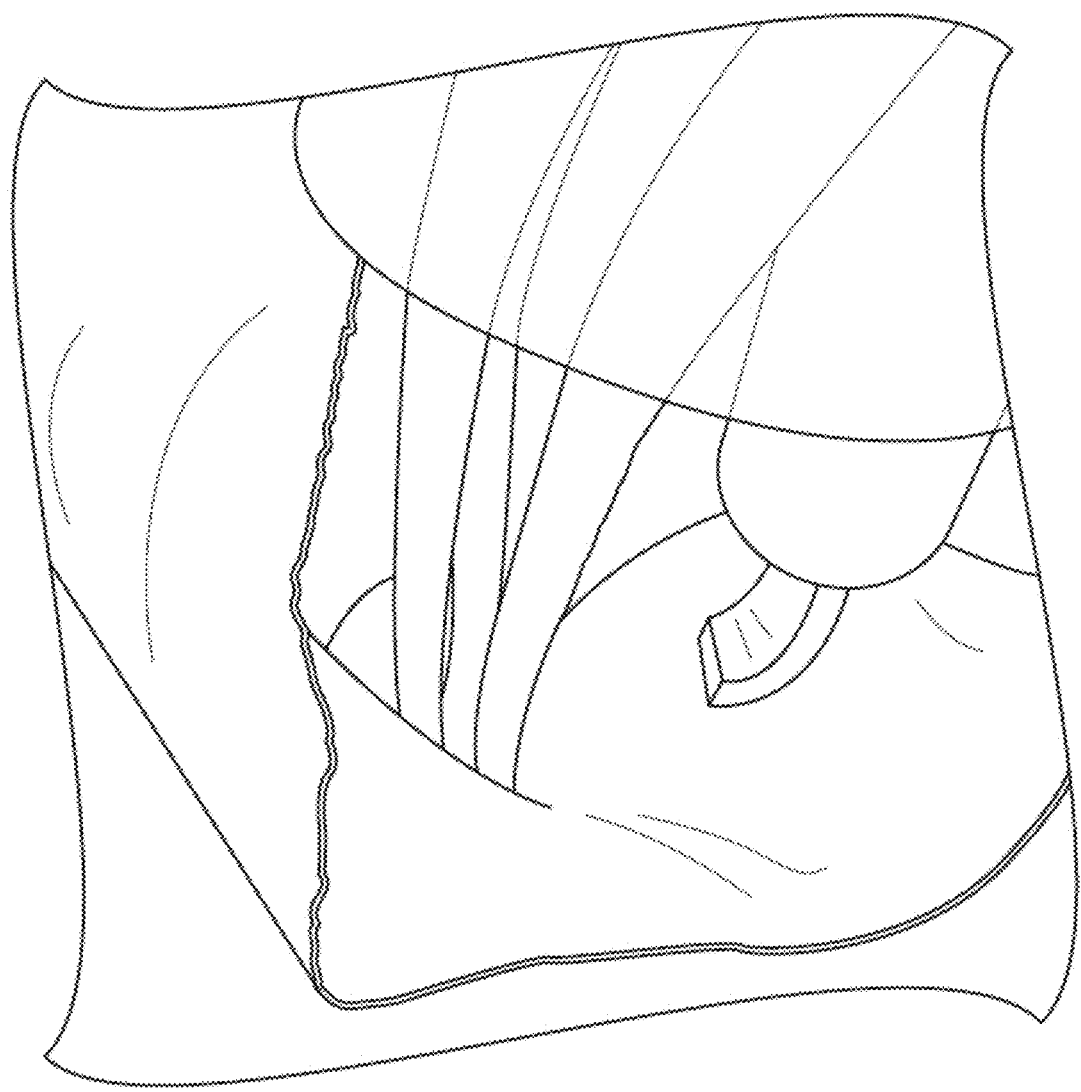
FIG. 1 illustrates with a suture in communication with a suture anchor extending through a patch, in accordance with the instant disclosure.

This disclosure is not limited to the particular systems, devices and methods described, as these may vary. The terminology used in the description is for the purpose of describing the particular versions or embodiments only, and is not intended to limit the scope of the disclosure.

The following terms shall have, for the purposes of this application, the respective meanings set forth below. Unless otherwise defined, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a," "an," and "the" include plural references, unless the context clearly dictates otherwise. Thus, for example, reference to a "fiber" is a reference to one or more fibers and equivalents thereof known to those skilled in the art, and so forth.

As used herein, the term "about" means plus or minus 10% of the numerical value of the number with which it is being used. Therefore, about 50 mm means in the range of 45 mm to 55 mm.

As used herein, the term "consists of" or "consisting of" means that the device or method includes only the elements, steps, or ingredients specifically recited in the particular claimed embodiment or claim.

In embodiments or claims where the term comprising is used as the transition phrase, such embodiments can also be envisioned with replacement of the term "comprising" with the terms "consisting of" or "consisting essentially of."

The terms "animal," "patient," and "subject" as used herein include, but are not limited to, humans and non-human vertebrates such as wild, domestic, and farm animals. In some embodiments, the terms "animal," "patient," and "subject" may refer to humans.

As used herein, the term "long axis," when referring to a tendon or ligament, describes the direction of the tendon or ligament sheath or, if the tendon or ligament does not comprise a sheath, then the axis formed by the connection between the bone and the tendon or ligament. The long axis of a tendon or ligament may also comprise the direction of the primary tensile structures, or the stress-bearing axis, of the tendon or ligament.

As used herein, the term "biocompatible" refers to non-harmful compatibility with living tissue. Biocompatibility is a broad term that describes a number of materials, including bioinert materials, bioactive materials, bioabsorbable materials, biostable materials, biotolerant materials, or any combination thereof.

The instant disclosure is directed to methods of improving bone-soft tissue healing using biocompatible electrospun polymer fibers. In one embodiment, a method may include locating a portion of a subject's bone, affixing a tendon or ligament to the bone using a hardware fixture, and placing a patch in physical communication with both the bone and the tendon or ligament, the patch comprising at least one electro spun polymer fiber. In some embodiments, the bone may be a humerus, and the tendon or ligament may be a supraspinatus tendon. In certain embodiments, the patch may comprise substantially parallel electrospun polymer fibers, and may be placed such that the fibers are also substantially parallel with the long axis of the tendon or ligament. In other embodiments, the fibers may be randomly oriented with respect to one another.

Electrospinning Fibers

Electrospinning is a method which may be used to process a polymer solution into a fiber. In embodiments wherein the diameter of the resulting fiber is on the nanometer scale, the fiber may be referred to as a nanofiber. Fibers may be formed into a variety of shapes by using a range of receiving surfaces, such as mandrels or collectors. In some embodiments, a flat shape, such as a sheet or sheet-like fiber mold, a fiber scaffold and/or tube, or a tubular lattice, may be formed by using a substantially round or cylindrical mandrel. In certain embodiments, the electrospun fibers may be cut and/or unrolled from the mandrel as a fiber mold to form the sheet. The resulting fiber molds or shapes may be used in many applications, including the repair or replacement of biological structures. In some embodiments, the resulting fiber scaffold may be implanted into a biological organism or a portion thereof.

Electrospinning methods may involve spinning a fiber from a polymer solution by applying a high DC voltage potential between a polymer injection system and a mandrel. In some embodiments, one or more charges may be applied to one or more components of an electrospinning system. In some embodiments, a charge may be applied to the mandrel, the polymer injection system, or combinations or portions thereof. Without wishing to be bound by theory, as the polymer solution is ejected from the polymer injection system, it is thought to be destabilized due to its exposure to a charge. The destabilized solution may then be attracted to a charged mandrel. As the destabilized solution moves from the polymer injection system to the mandrel, its solvents may evaporate and the polymer may stretch, leaving a long, thin fiber that is deposited onto the mandrel. The polymer solution may form a Taylor cone as it is ejected from the polymer injection system and exposed to a charge.

In certain embodiments, a first polymer solution comprising a first polymer and a second polymer solution comprising a second polymer may each be used in a separate polymer injection system at substantially the same time to produce one or more electrospun fibers comprising the first polymer interspersed with one or more electrospun fibers comprising the second polymer. Such a process may be referred to as "co-spinning" or "co-electrospinning," and a scaffold produced by such a process may be described as a co-spun or co-electrospun scaffold.

Polymer Injection System

A polymer injection system may include any system configured to eject some amount of a polymer solution into an atmosphere to permit the flow of the polymer solution from the injection system to the mandrel. In some embodiments, the polymer injection system may deliver a continuous or linear stream with a controlled volumetric flow rate of a polymer solution to be formed into a fiber. In some embodiments, the polymer injection system may deliver a variable stream of a polymer solution to be formed into a fiber. In some embodiments, the polymer injection system may be configured to deliver intermittent streams of a polymer solution to be formed into multiple fibers. In some embodiments, the polymer injection system may include a syringe under manual or automated control. In some embodiments, the polymer injection system may include multiple syringes and multiple needles or needle-like components under individual or combined manual or automated control. In some embodiments, a multi-syringe polymer injection system may include multiple syringes and multiple needles or needle-like components, with each syringe containing the same polymer solution. In some embodiments, a multi-syringe polymer injection system may include multiple syringes and multiple needles or needle-like components, with each syringe containing a different polymer solution. In some embodiments, a charge may be applied to the polymer injection system, or to a portion thereof. In some embodiments, a charge may be applied to a needle or needle-like component of the polymer injection system.

In some embodiments, the polymer solution may be ejected from the polymer injection system at a flow rate of less than or equal to about 5 mL/h per needle. In other embodiments, the polymer solution may be ejected from the polymer injection system at a flow rate per needle in a range from about 0.01 mL/h to about 50 mL/h. The flow rate at which the polymer solution is ejected from the polymer injection system per needle may be, in some non-limiting examples, about 0.01 mL/h, about 0.05 mL/h, about 0.1 mL/h, about 0.5 mL/h, about 1 mL/h, about 2 mL/h, about 3 mL/h, about 4 mL/h, about 5 mL/h, about 6 mL/h, about 7 mL/h, about 8 mL/h, about 9 mL/h, about 10 mL/h, about 11 mL/h, about 12 mL/h, about 13 mL/h, about 14 mL/h, about 15 mL/h, about 16 mL/h, about 17 mL/h, about 18 mL/h, about 19 mL/h, about 20 mL/h, about 21 mL/h, about 22 mL/h, about 23 mL/h, about 24 mL/h, about 25 mL/h, about 26 mL/h, about 27 mL/h, about 28 mL/h, about 29 mL/h, about 30 mL/h, about 31 mL/h, about 32 mL/h, about 33 mL/h, about 34 mL/h, about 35 mL/h, about 36 mL/h, about 37 mL/h, about 38 mL/h, about 39 mL/h, about 40 mL/h, about 41 mL/h, about 42 mL/h, about 43 mL/h, about 44 mL/h, about 45 mL/h, about 46 mL/h, about 47 mL/h, about 48 mL/h, about 49 mL/h, about 50 mL/h, or any range between any two of these values, including endpoints.

As the polymer solution travels from the polymer injection system toward the mandrel, the diameter of the resulting fibers may be in the range of about 0.1 µm to about 10 µm. Some non-limiting examples of electrospun fiber diameters may include about 0.1 µm, about 0.2 µm, about 0.25 µm, about 0.5 µm, about 1 µm, about 2 µm, about 5 µm, about 10 µm, about 20 µm, or ranges between any two of these values, including endpoints. In some embodiments, the electrospun fiber diameter may be from about 0.25 µm to about 20 µm.

Polymer Solution

In some embodiments, the polymer injection system may be filled with a polymer solution. In some embodiments, the polymer solution may comprise one or more polymers. In some embodiments, the polymer solution may be a fluid formed into a polymer liquid by the application of heat. A polymer solution may include, for example, non-resorbable polymers, resorbable polymers, natural polymers, or a combination thereof.

In some embodiments, the polymers may include, for example, polyethylene terephthalate, polyurethane, polyethylene, polyethylene oxide, polyester, polymethylmethacrylate, polyacrylonitrile, silicone, polycarbonate, polyether ketone ketone, polyether ether ketone, polyether imide, polyamide, polystyrene, polyether sulfone, polysulfone, polyvinyl acetate, polytetrafluoroethylene, polyvinylidene fluoride, polycaprolactone, polylactic acid, polyglycolic acid, polylactide-co-glycolide, polylactide-co-caprolactone, polyglycerol sebacate, polydioxanone, polyhydroxybutyrate, poly-4-hydroxybutyrate), trimethylene carbonate, polydiols, polyesters, collagen, gelatin, fibrin, fibronectin, albumin, hyaluronic acid, elastin, chitosan, alginate, silk, copolymers thereof, and combinations thereof.

It may be understood that polymer solutions may also include a combination of one or more of non-resorbable, resorbable polymers, and naturally occurring polymers in any combination or compositional ratio. In an alternative embodiment, the polymer solutions may include a combination of two or more non-resorbable polymers, two or more resorbable polymers or two or more naturally occurring polymers. In some non-limiting examples, the polymer solution may comprise a weight percent ratio of, for example, from about 5% to about 90%. Non-limiting examples of such weight percent ratios may include about 5%, about 10%, about 15%, about 20%, about 25%, about 30%, about 33%, about 35%, about 40%, about 45%, about 50%, about 55%, about 60%, about 66%, about 70%, about 75%, about 80%, about 85%, about 90%, or ranges between any two of these values, including endpoints.

In some embodiments, the polymer solution may comprise one or more solvents. In some embodiments, the solvent may comprise, for example, acetone, dimethylformamide, dimethylsulfoxide, N-methylpyrrolidone, N,N-dimethylformamide, Nacetonitrile, hexanes, ether, dioxane, ethyl acetate, pyridine, toluene, xylene, tetrahydrofuran, trifluoroacetic acid, hexafluoroisopropanol, acetic acid, dimethylacetamide, chloroform, dichloromethane, water, alcohols, ionic compounds, or combinations thereof. The concentration range of polymer or polymers in solvent or solvents may be, without limitation, from about 1 wt % to about 50 wt %. Some non-limiting examples of polymer concentration in solution may include about 1 wt %, 3 wt %, 5 wt %, about 10 wt %, about 15 wt %, about 20 wt %, about 25 wt %, about 30 wt %, about 35 wt %, about 40 wt %, about 45 wt %, about 50 wt %, or ranges between any two of these values, including endpoints.

In some embodiments, the polymer solution may also include additional materials. Non-limiting examples of such additional materials may include radiation opaque materials, contrast agents, electrically conductive materials, fluorescent materials, luminescent materials, antibiotics, growth factors, vitamins, cytokines, steroids, anti-inflammatory drugs, small molecules, sugars, salts, peptides, proteins, cell factors, DNA, RNA, other materials to aid in non-invasive imaging, or any combination thereof. In some embodiments, the radiation opaque materials may include, for example, barium, tantalum, tungsten, iodine, gadolinium, gold, platinum, bismuth, or bismuth (III) oxide. In some embodiments, the electrically conductive materials may include, for example, gold, silver, iron, or polyaniline.

In some embodiments, the additional materials may be present in the polymer solution in an amount from about 1 wt % to about 1500 wt % of the polymer mass. In some non-limiting examples, the additional materials may be present in the polymer solution in an amount of about 1 wt %, about 5 wt %, about 10 wt %, about 15 wt %, about 20 wt %, about 25 wt %, about 30 wt %, about 35 wt %, about 40 wt %, about 45 wt %, about 50 wt %, about 55 wt %, about 60 wt %, about 65 wt %, about 70 wt %, about 75 wt %, about 80 wt %, about 85 wt %, about 90 wt %, about 95 wt %, about 100 wt %, about 125 wt %, about 150 wt %, about 175 wt %, about 200 wt %, about 225 wt %, about 250 wt %, about 275 wt %, about 300 wt %, about 325 wt %, about 350 wt %, about 375 wt %, about 400 wt %, about 425 wt %, about 450 wt %, about 475 wt %, about 500 wt %, about 525 wt %, about 550 wt %, about 575 wt %, about 600 wt %, about 625 wt %, about 650 wt %, about 675 wt %, about 700 wt %, about 725 wt %, about 750 wt %, about 775 wt %, about 800 wt %, about 825 wt %, about 850 wt %, about 875 wt %, about 900 wt %, about 925 wt %, about 950 wt %, about 975 wt %, about 1000 wt %, about 1025 wt %, about 1050 wt %, about 1075 wt %, about 1100 wt %, about 1125 wt %, about 1150 wt %, about 1175 wt %, about 1200 wt %, about 1225 wt %, about 1250 wt %, about 1275 wt %, about 1300 wt %, about 1325 wt %, about 1350 wt %, about 1375 wt %, about 1400 wt %, about 1425 wt %, about 1450 wt %, about 1475 wt %, about 1500 wt %, or any range between any of these two values, including endpoints. In one embodiment, the polymer solution may include tantalum present in an amount of about 10 wt % to about 1,500 wt %.

The type of polymer in the polymer solution may determine the characteristics of the electrospun fiber. Some fibers may be composed of polymers that are bio-stable and not absorbable or biodegradable when implanted. Such fibers may remain generally chemically unchanged for the length of time in which they remain implanted. Alternatively, fibers may be composed of polymers that may be absorbed or bio-degraded over time. Such fibers may act as an initial template or scaffold during a healing process. These templates or scaffolds may degrade in vivo once the tissues have a degree of healing by natural structures and cells. It may be further understood that a polymer solution and its resulting electrospun fiber(s) may be composed or more than one type of polymer, and that each polymer therein may have a specific characteristic, such as bio-stability or biodegradability.

Applying Charges to Electrospinning Components

In an electrospinning system, one or more charges may be applied to one or more components, or portions of components, such as, for example, a mandrel or a polymer injection system, or portions thereof. In some embodiments, a positive charge may be applied to the polymer injection system, or portions thereof. In some embodiments, a negative charge may be applied to the polymer injection system, or portions thereof. In some embodiments, the polymer injection system, or portions thereof, may be grounded. In some embodiments, a positive charge may be applied to mandrel, or portions thereof. In some embodiments, a negative charge may be applied to the mandrel, or portions thereof. In some embodiments, the mandrel, or portions thereof, may be grounded. In some embodiments, one or more components or portions thereof may receive the same charge. In some embodiments, one or more components, or portions thereof, may receive one or more different charges.

The charge applied to any component of the electrospinning system, or portions thereof, may be from about −15 kV to about 30 kV, including endpoints. In some non-limiting examples, the charge applied to any component of the electrospinning system, or portions thereof, may be about −15 kV, about −10 kV, about −5 kV, about −4 kV, about −3 kV, about −1 kV, about −0.01 kV, about 0.01 kV, about 1 kV, about 5 kV, about 10 kV, about 11 kV, about 11.1 kV, about 12 kV, about 15 kV, about 20 kV, about 25 kV, about 30 kV, or any range between any two of these values, including endpoints. In some embodiments, any component of the electrospinning system, or portions thereof, may be grounded.

Mandrel Movement During Electrospinning

During electrospinning, in some embodiments, the mandrel may move with respect to the polymer injection system. In some embodiments, the polymer injection system may move with respect to the mandrel. The movement of one electrospinning component with respect to another electrospinning component may be, for example, substantially rotational, substantially translational, or any combination thereof. In some embodiments, one or more components of the electrospinning system may move under manual control. In some embodiments, one or more components of the electrospinning system may move under automated control. In some embodiments, the mandrel may be in contact with or mounted upon a support structure that may be moved using one or more motors or motion control systems. The pattern of the electrospun fiber deposited on the mandrel may depend upon the one or more motions of the mandrel with respect to the polymer injection system. In some embodiments, the mandrel surface may be configured to rotate about its long axis. In one non-limiting example, a mandrel having a rotation rate about its long axis that is faster than a translation rate along a linear axis, may result in a nearly helical deposition of an electrospun fiber, forming windings about the mandrel. In another example, a mandrel having a translation rate along a linear axis that is faster than a rotation rate about a rotational axis, may result in a roughly linear deposition of an electrospun fiber along a liner extent of the mandrel.

Methods of Improving Bone-Soft Tissue Healing

The instant disclosure is directed to methods of improving bone-soft tissue healing using biocompatible electrospun polymer fibers. It may be understood that the methods described herein may be applied to any bone-soft tissue interface, and that the tendon-bone and ligament-bone interface examples described herein are non-limiting.

Without wishing to be bound by theory, during surgery, the debridement of at least a portion of a subject's bone near the area where the soft tissue is meant to be reattached may induce bleeding, thereby increasing the number of healing and growth factors in the localized area. Such an increase may promote healing at the bone-soft tissue interface. In some embodiments, the use of a patch comprising one or more electrospun polymer fibers may further improve healing at the interface, perhaps by providing a matrix for the cells to attach, or perhaps by facilitating the migration of cells from healthy tissues to the repair site. In certain embodiments, aligning the electrospun polymer fibers with the long axis of the soft tissue to be repaired may further facilitate such migration. In other embodiments, randomly aligned electrospun polymer fibers may be sufficient to facilitate cell migration and interface healing. Debridement is an optional step of the methods described herein.

In some embodiments, the methods described herein may also contribute to the healing and/or reformation of Sharpey's fibers, which are fibrous portions of bone tissue that may serve to anchor soft tissue to bone during healing at a bone-soft tissue interface. Without wishing to be bound by theory, the electrospun polymer fiber constructs described herein may serve to improve the speed and/or strength of the formation and/or reestablishment of Sharpey's fibers at the bone-soft tissue interface. In some embodiments, a patch comprising substantially parallel electrospun polymer fibers may help form or restore Sharpey's fibers, and/or may increase the rate at which such fibers are formed or restored at a bone-soft tissue interface. In other embodiments, a patch comprising randomly oriented electrospun polymer fibers may help form or restore Sharpey's fibers, and/or may increase the rate at which such fibers are formed or restored at a bone-soft tissue interface. In some embodiments, a patch comprising a combination of randomly oriented and substantially parallel electrospun polymer fibers may help restore Sharpey's fibers, and/or may increase the rate at which such fibers are formed or restored at a bone-soft tissue interface. In some embodiments, any of the patches described herein may help form or restore Sharpey's fibers at the bone-soft tissue interface that may comprise substantially the same density as those found in original, uninjured bone-soft tissue interfaces.

In one embodiment, a method may comprise locating at least a portion of a subject's bone, affixing a tendon or ligament to the bone using a hardware fixture, and placing a patch in physical communication with both the bone and the tendon or ligament, the patch comprising at least one electrospun polymer fiber. In some embodiments, the method may consist only of these steps. In certain embodiments, locating at least a portion of a subject's bone may further comprise debriding at least a portion of the subject's bone.

In some embodiments, the hardware fixture may comprise a suture in physical communication with a suture anchor. In other embodiments, the hardware fixture may comprise a screw, an interference screw, an anchor that does not include a suture, or any equivalent hardware fixtures known for use in orthopedics.

In some embodiments, the patch may be in physical communication with the portion of the subject's bone that has been debrided. In certain embodiments, the patch may comprise substantially parallel electrospun polymer fibers, and may be placed such that the fibers are also substantially parallel with the long axis of the tendon or ligament. In other embodiments, the patch pay comprise randomly oriented electrospun polymer fibers. In still other embodiments, the patch may comprise a combination of randomly oriented and substantially parallel electrospun polymer fibers. In some embodiments, the patch may be positioned at a healing interface between the bone and the tendon or ligament.

Figure 2:
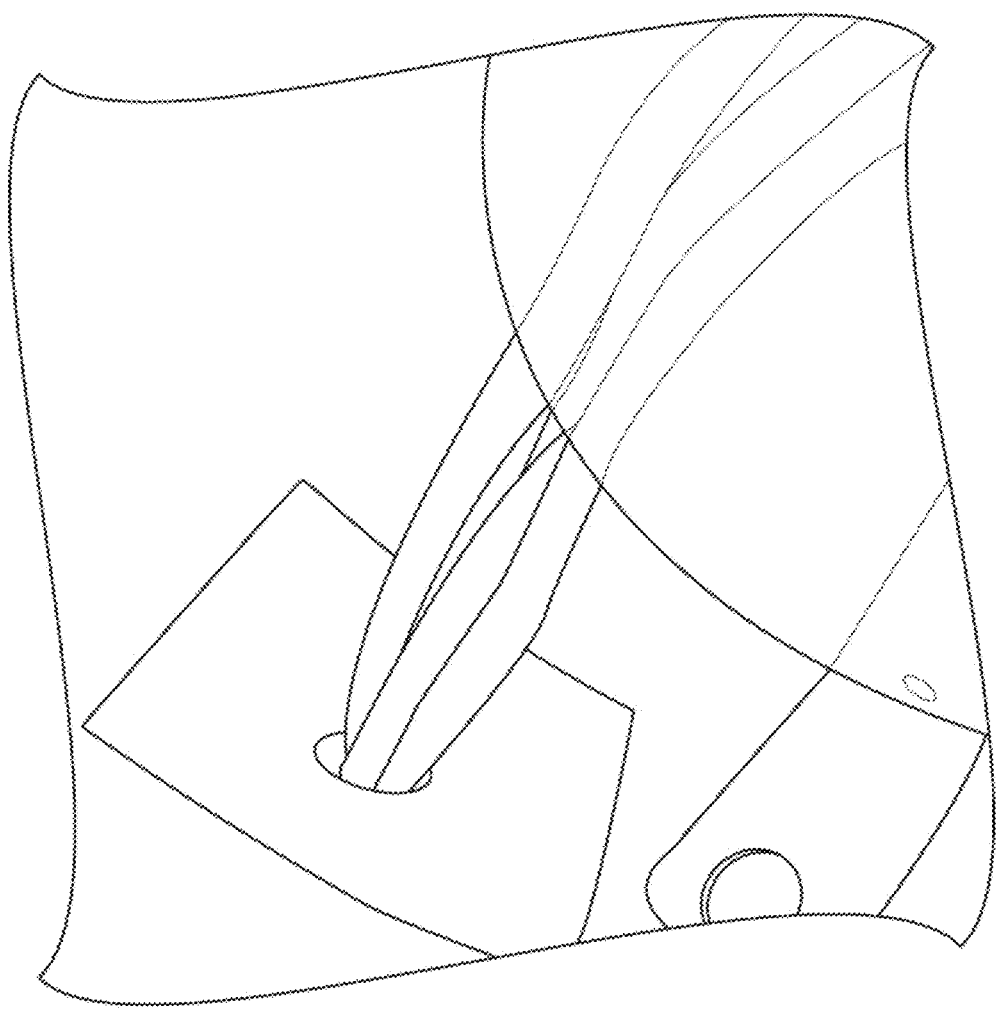
FIG. 2 illustrates an alternative view of a suture in communication with a suture anchor extending through a patch, in accordance with the instant disclosure.

In some embodiments, the suture may comprise one or more sutures. In some embodiments, the one or more sutures may extend through the patch. FIG. 1 and FIG. 2 illustrate embodiments of a suture in communication with a suture anchor (not shown) extending through a patch. In another embodiment, the one or more sutures may extend through an opening in the patch. In some embodiments, the patch may surround or substantially surround the area from which the one or more sutures extends. In another embodiment, the one or more sutures may extend from approximately the center of the patch.

In some embodiments, the bone may be, for example, a humerus, a radius, an ulna, a tibia, a femur, a calcaneus, or any combination thereof. In one embodiment, the bone is a humerus. In another embodiment, the bone is selected from a femur and a tibia.

In some embodiments, the tendon or ligament may be, for example, a supraspinatus tendon, an infraspinatus tendon, a subscapularis tendon, a deltoid tendon, a biceps tendon, a triceps tendon, an anterior cruciate ligament, a posterior cruciate ligament, a medial collateral ligament, a lateral collateral ligament, an illiotibial band, a quadriceps tendon, a hamstring tendon, a sartorius tendon, an Achilles tendon, a tibialis anterior tendon, or any combination thereof. In one embodiment, the tendon or ligament is a supraspinatus tendon. In another embodiment, the tendon or ligament is an anterior cruciate ligament.

In some embodiments, the patch may comprise one or more electrospun polymer fibers. In certain embodiments, the electrospun polymer fibers may have a diameter in the range of about 0.1 µm to about 10 µm. Some non-limiting examples of electrospun fiber diameters may include about 0.1 µm, about 0.2 µm, about 0.25 µm, about 0.5 µm, about 1 µm, about 2 µm, about 3 µm, about 4 µm, about 5 µm, about 6 µm, about 7 µm, about 8 µm, about 9 µm, about 10 µm, about 11 µm, about 12 µm, about 13 µm, about 14 µm, about 15 µm, about 16 µm, about 17 µm, about 18 µm, about 19 µm, about 20 µm, or ranges between any two of these values, including endpoints. In some embodiments, the electrospun fiber diameter may be from about 0.25 µm to about 20 µm.

In some embodiments, the patch may have, independently, a length from about 1 mm to about 100 mm, and a width from about 1 mm to about 100 mm. The patch may have, independently, a length or width of about, for example, about 1 mm, about 5 mm, about 10 mm, about 15 mm, about 20 mm, about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, about 95 mm, about 100 mm, or any range between any two of these values, including endpoints.

In some embodiments, the patch may have a thickness from about 100 µm to about 5,000 µm. The patch may have a thickness of, for example, about 100 µm, about 200 µm, about 300 µm, about 400 µm, about 500 µm, about 600 µm, about 700 µm, about 800 µm, about 900 µm, about 1,000 µm, about 1,250 µm, about 1,500 µm, about 1,750 µm, about 2,000 µm, about 2,250 µm, about 2,500 µm, about 2,750 µm, about 3,000 µm, about 3,250 µm, about 3,500 µm, about 3,750 µm, about 4,000 µm, about 4,250 µm, about 4,500 µm, about 4,750 µm, about 5,000 µm, or any range between any two of these values, including endpoints.

In some embodiments, the patch may comprise one or more pores. In certain embodiments, the pores are uniformly, or substantially uniformly, distributed throughout the patch, while in other embodiments the pores are irregularly distributed within the patch. In some embodiments, the pores may have a diameter from about 0.25 µm to about 50 µm. The diameter of the pores may be, for example, about 0.25 µm, about 0.5 µm, about 1 µm, about 2 µm, about 3 µm, about 4 µm, about 5 µm, about 10 µm, about 15 µm, about 20 µm, about 25 µm, about 30 µm, about 35 µm, about 40 µm, about 45 µm, about 50 µm, or any range between any two of these values, including endpoints.

In some embodiments, the patch may have particular mechanical properties, such as a particular Young's modulus, suture retention strength, radial stiffness, or bursting strength. In some embodiments, the Young's modulus of the patch may be from about 0.5 MPa to about 1,000 MPa. The Young's modulus may be, for example, about 0.5 MPA, about 1 MPa, about 10 MPa, about 20 MPa, about 30 MPa, about 40 MPa, about 50 MPa, about 60 MPa, about 70 MPa, about 80 MPa, about 90 MPa, about 100 MPa, about 110 MPa, about 120 MPa, about 130 MPa, about 140 MPa, about 150 MPa, about 160 MPa, about 170 MPa, about 180 MPa, about 190 MPa, about 200 MPa, about 210 MPa, about 220 MPa, about 230 MPa, about 240 MPa, about 250 MPa, about 260 MPa, about 270 MPa, about 280 MPa, about 290 MPa, about 300 MPa, about 310 MPa, about 320 MPa, about 330 MPa, about 340 MPa, about 350 MPa, about 360 MPa, about 370 MPa, about 380 MPa, about 390 MPa, about 400 MPa, about 410 MPa, about 420 MPa, about 430 MPa, about 440 MPa, about 450 MPa, about 460 MPa, about 470 MPa, about 480 MPa, about 490 MPa, about 500 MPa, about 510 MPa, about 520 MPa, about 530 MPa, about 540 MPa, about 550 MPa, about 560 MPa, about 570 MPa, about 580 MPa, about 590 MPa, about 600 MPa, about 610 MPa, about 620 MPa, about 630 MPa, about 640 MPa, about 650 MPa, about 660 MPa, about 670 MPa, about 680 MPa, about 690 MPa, about 700 MPa, about 710 MPa, about 720 MPa, about 730 MPa, about 740 MPa, about 750 MPa, about 760 MPa, about 770 MPa, about 780 MPa, about 790 MPa, about 800 MPa, about 810 MPa, about 820 MPa, about 830 MPa, about 840 MPa, about 850 MPa, about 860 MPa, about 870 MPa, about 880 MPa, about 890 MPa, about 900 MPa, about 910 MPa, about 920 MPa, about 930 MPa, about 940 MPa, about 950 MPa, about 960 MPa, about 970 MPa, about 980 MPa, about 990 MPa, about 1,000 MPa, or any range between any two of these values, including endpoints.

In some embodiments, the patch may comprise at least one layer of electrospun polymer fibers that are substantially parallel with respect to one another. In some embodiments, the patch may comprise more than one layer, and the electrospun polymer fibers of a first layer may be substantially parallel with respect to one another and substantially parallel to the fibers of any additional layers. In other embodiments, the patch may comprise more than one layer, and the electrospun polymer fibers of a first layer may be substantially parallel with respect to one another and substantially perpendicular to the fibers of any additional layers. A layer may include a sheet, such that a first layer may comprise a first sheet, and a second layer may comprise a second sheet, and so on, similar to how textiles may include more than one layer of material.

In some embodiments, the patch may be placed such that the substantially parallel electrospun polymer fibers are substantially parallel with the long axis of the tendon or ligament to be repaired. In some embodiments, the substantially parallel electrospun polymer fibers and, optionally, their alignment with the long axis of the tendon or ligament to be repaired, may be configured to facilitate the migration of cells to the site of the repair.

In some embodiments, the patch may further comprise additional materials. The additional materials may be, for example, tricalcium phosphate, hydroxyapatite, bioglass, or any combination thereof.

In additional embodiments, the patch may further comprise a biologic component. The biologic component may be, for example, mesenchymal stem cells, tenocytes, fibroblasts, osteoblasts, platelet-rich plasma, bone marrow aspirate, stromal vascular fraction, bursa cells, amnion, growth factors, or any combination thereof.

In some embodiments, the at least one electrospun polymer fiber may comprise a polymer selected from the group consisting of polyethylene terephthalate, polyurethane, polyethylene, polyethylene oxide, polyester, polymethylmethacrylate, polyacrylonitrile, silicone, polycarbonate, polyether ketone ketone, polyether ether ketone, polyether imide, polyamide, polystyrene, polyether sulfone, polysulfone, polyvinyl acetate, polytetrafluoroethylene, polyvinylidene fluoride, polycaprolactone, polylactic acid, polyglycolic acid, polylactide-co-glycolide, polylactide-co-caprolactone, polyglycerol sebacate, polydioxanone, polyhydroxybutyrate, poly-4-hydroxybutyrate), trimethylene carbonate, polydiols, polyesters, collagen, gelatin, fibrin, fibronectin, albumin, hyaluronic acid, elastin, chitosan, alginate, silk, copolymers thereof, or any combination thereof. In some embodiments, the at least one electrospun polymer fiber may comprise a co-spun combination of about 20 wt % of fibers comprising polyethylene terephthalate and about 80 wt % of fibers comprising polyurethane. In other embodiments, the at least one electrospun polymer fiber may comprise a co-spun combination of about 50 wt % of fibers comprising polylactide-co-caprolactone fibers and about 50 wt % of fibers comprising polyglycolic acid. In still other embodiments, the at least one electrospun polymer fiber may comprise at least a first fiber comprising polylactide-co-caprolactone and at least a second fiber comprising polyglycolic acid, wherein the first fiber and the second fiber are co-spun (sometimes referred to as "co-electrospun").

In another embodiment, a method may comprise locating a humerus of a subject, affixing a supraspinatus tendon to the humerus using a suture anchor in physical communication with a suture, and placing a patch comprising at least one electrospun polymer fiber in physical communication with the humerus and the supraspinatus tendon, such that the patch is between the humerus and the supraspinatus tendon, and the suture extends through an opening in the patch. In one embodiment, the method consists of only these steps. In other embodiments, the step of locating a humerus of a subject may further comprise debriding at least a portion of the humerus of the subject.

EXAMPLES

Example 1

Ovine Rotator Cuff Repair Model

The objective of this study was to examine the bone ingrowth, local tissue response, and biomechanical effectiveness of repair of the rotator cuff with embodiments of the scaffolds and methods described herein in an ovine (sheep) model. Forty animals were divided into two groups: a treatment group (20 animals), which was treated with a scaffold as described herein, and a control group (20 animals), which underwent rotator cuff repairs, but did not receive a scaffold. The contralateral untreated shoulders of 10 animals were collected and used as untreated samples.

In the treatment and control groups, the right infraspinatus tendon was completely transected at the humeral attachment and acutely reattached to the humeral footprint using a total of four suture anchors. In the treatment group, a scaffold was sandwiched between the infraspinatus tendon and humeral footprint. Ten animals from each group were sacrificed 6 weeks after the repair, and the remaining ten animals from each group were sacrificed 12 weeks after the repair.

Of the 10 animals in each group sacrificed at 6 weeks, 5 animals in each group were processed for biomechanical testing of the strength of the repair, and the other 5 animals in each group were processed for histology of the bone-tendon interface. Of the 10 animals in each group sacrificed at 12 weeks, 5 animals in each group were processed for biomechanical testing of the strength of the repair, and 5 animals were processed for histology of the bone-tendon interface as well as overall organ pathology assessment. In addition, the contralateral untreated shoulders of 10 animals were collected and used as untreated samples. Of those ten contralateral untreated shoulders, 5 were processed for biomechanical testing of the strength of the unrepaired rotator cuff, and the other 5 were processed for histology of the bone-tendon interface.

Gross dissection was completed at necropsy for each animal. Fresh humerus-infraspinatus tendon constructs were delivered to a bioengineering research laboratory within hours of animal sacrifice, accompanied by a necropsy record. The extraneous soft tissue was removed from each shoulder. Samples were digitally imaged and radiographed. Samples slated for histological analysis were placed in 10% neutral buffered formalin.

Samples slated for biomechanical analysis underwent testing in two phases: (A) preconditioning, and (B) ramp to failure. Ramp to failure was performed last because it is a destructive test. All loads imparted on the samples were applied quasi-statically and aligned collinear to the physiologic loading direction of the tendon. Each ovine infraspinatus tendon-humerus bone construct was mounted in a mechanical testing (MTS) system prior to biomechanical assessment. High-contrast reflective markers were attached to the tendon, segmenting three regions of interest (ROIs) within the tendon: proximal, middle, and distal to the surgical repair site. Digital image correlation was used to track 2D contrast marker displacement during loading.

(A) Preconditioning: To minimize the viscoelastic effects on the measured biomechanical response, ten cyclic tensile loads ranging between 0 and 2% strain were applied to precondition the tendon. The preconditioning phase was preceded by a ~2 minute preload phase. A static preload of 10 N was applied to all specimens for ~2 minutes or until the specimen was fully relaxed. The sample's reference gauge length was measured as the tendon's distance, in millimeters, from the bottom of the cryo-clamp's grip to the tendon's insertion into the humerus following the 10 N preload.

(B) Ramp to failure: To characterize structural and material properties of the repaired tissue, the specimens were quasi-statically loaded to failure at a rate of 0.5% strain/sec. Load and displacement data were acquired at 25 Hz (due to slow loading rate and to allow registration with the DIC data). Digital videos were collected at 25 Hz during ramp to failure testing for DIC analysis. Digital photographs were taken of each specimen after failure to document the location and mode of failure (MOF). Photographs identified the Animal ID Number and Study Identification Number (at a minimum).

Structural properties representing the biomechanical behavior of the bone-tendon construct and material properties representing the biomechanical behavior at the tissue level were calculated. Force (N) and displacement (mm) data were used to characterize structural properties, including ultimate load (N) and stiffness (N/mm). Material properties were calculated from structural measurements by normalization to cross-sectional area or to the initial gauge length of the sample. Material property calculations included ultimate stress (MPa), ultimate strain (mm/mm), and elastic modulus (MPa). 2D displacements of the reflective markers adhered to the tendon were tracked throughout ramp to failure testing to determine the localized strain in the tendon at ultimate load, using digital image correlation. Localized strain (mm/mm) at the ultimate load was calculated for three discrete regions of interest (ROI): (i) proximal ROI (i.e. the region spanning the original surgery site); (ii) middle ROI (i.e. the region adjacent to the original surgery site); and (iii) distal ROI (i.e. the region encompassing the mid-substance of the tendon). Mode of failure (MOF) was also calculated. Possible modes of failure included (a) failure at the repair site; (b) mid-substance failure, (c) bone avulsion; and (d) failure at the repair site and mid-substance failure (i.e. a mixed failure mode).

As described above, ten (treatment group n=5; control group n=5) animals were allocated for histological analysis per sacrifice time point. Organs of interest were also collected from the animals sacrificed at 12 weeks, and were placed in 10% neutral buffered formalin for fixation prior to histology processing.

Following gross dissection and fixation (including a minimum of two weeks in formalin), samples were bisected through the infraspinatus and humeral attachment sites, creating a slab of tissue in the sagittal plane containing the humerus+bone anchor(s), repair site (i.e., the footprint) and surrounding tendon soft tissue(s). Images of the gross tissue blocks were taken. After fixation, the tissue was dehydrated in graded solutions of ETOH on a tissue processor. After processing, the samples were cleared with acetone and polymerized into a hardened plastic block using Hard Acrylosin.

Histological sections were taken in the sagittal plane to display the humerus+bone anchor(s), repair site (i.e., the footprint) and surrounding soft tissue. Three slide sections were cut through each ROI. Initial sections were taken using a diamond blade bone saw at a thickness of approximately 300-400 µm. All sections were ground using a microgrinder to 60-70 µm thickness and stained. Sections were first stained with Sanderson's Rapid bone stain, which provides differentiation of cells within the section and allows detection of cartilage within the tissue. Slides were then counterstained using a Van Gieson bone stain that allows differentiation of collagen and detection of bone (immature woven bone and mature lamellar bone) within the section.

2 time points×2 treatment groups (treatment and control)×5 samples per group×2 slides per group yielded a total of 40 slides from the surgically treated samples (i.e. 20 slides from the treatment group and 20 slides from the control group). Five contralateral shoulders (untreated controls) were also allocated for slide production, and yielded 2 slides per ROI for a total of 10 untreated slides.

High-resolution digital images were acquired by field for the all surgical site slides using a Nikon E800 microscope, a Spot digital camera, and a Pentium IBM-based computer with expanded memory capabilities. Organ slides were not imaged.

Image Pro software was used for histomorphometric measurements on the anchor-bone ROIs. Histomorphometric measurements were performed on calibrated digital images to quantify: (i) percent bone area within the ROI; (ii) percent fibrous tissue within the ROI; and (iii) percent implant area within the ROI.

Slides were delivered to a certified pathologist for histopathology analysis. The outcome data included a quantitative scoring of the following parameters: (i) cellular analysis; (ii) inflammatory/foreign analysis; (iii) fiber alignment; (iv) implant degradation; (v) osteoblast/osteoclast activity; (vi) osteogenic response; and (vii) comparison to untreated samples (shoulder surgical site slides only).

Figure 3A:
FIG. 3A illustrates a histological sample of a native ovine rotator cuff.
Figure 3B:
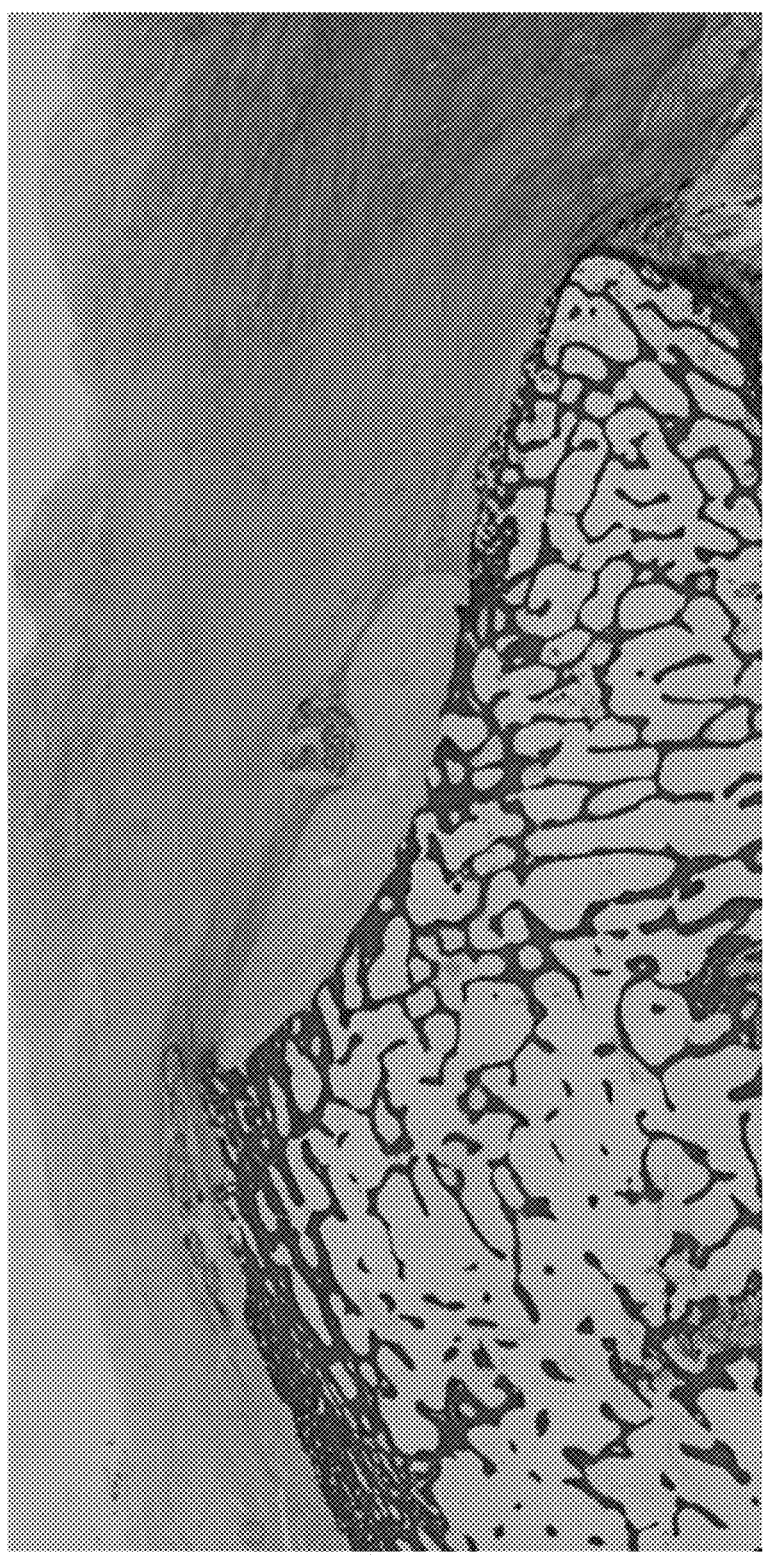
FIG. 3B illustrates a histological sample of an ovine rotator cuff, at 6 weeks, repaired without using a scaffold in accordance with the instant disclosure.
Figure 3C:
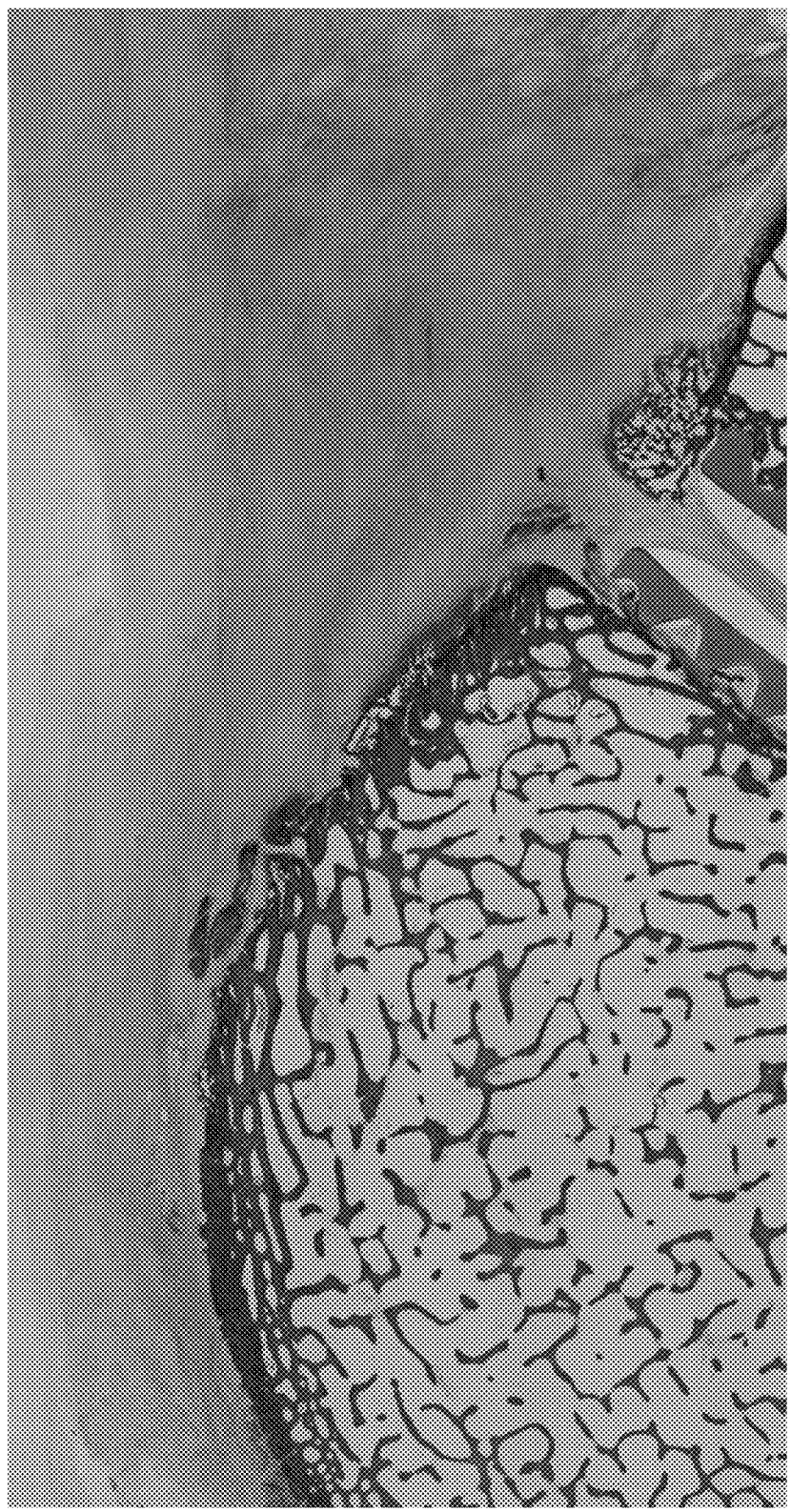
FIG. 3C illustrates a histological sample of an ovine rotator cuff, at 6 weeks, repaired with a scaffold in accordance with the instant disclosure.

FIG. 3A illustrates a histological sample of an untreated control rotator cuff (i.e. a contralateral control). FIG. 3B illustrates a histological sample of a treated control rotator cuff at 6 weeks (i.e. a rotator cuff that underwent a repair but did not receive a scaffold as described herein). FIG. 3C illustrates a histological sample of a treated rotator cuff at 6 weeks (i.e. a rotator cuff that underwent a repair and received a scaffold as described herein). This histology illustrates a fibrous scar between the bone and tendon with the suture repair in the samples repaired without a scaffold (e.g. FIG. 3B). Such a scar was not present in the samples repaired with a scaffold as described herein (e.g. FIG. 3C).

Figure 4A:
FIG. 4A illustrates a histological sample of a native ovine rotator cuff.
Figure 4B:
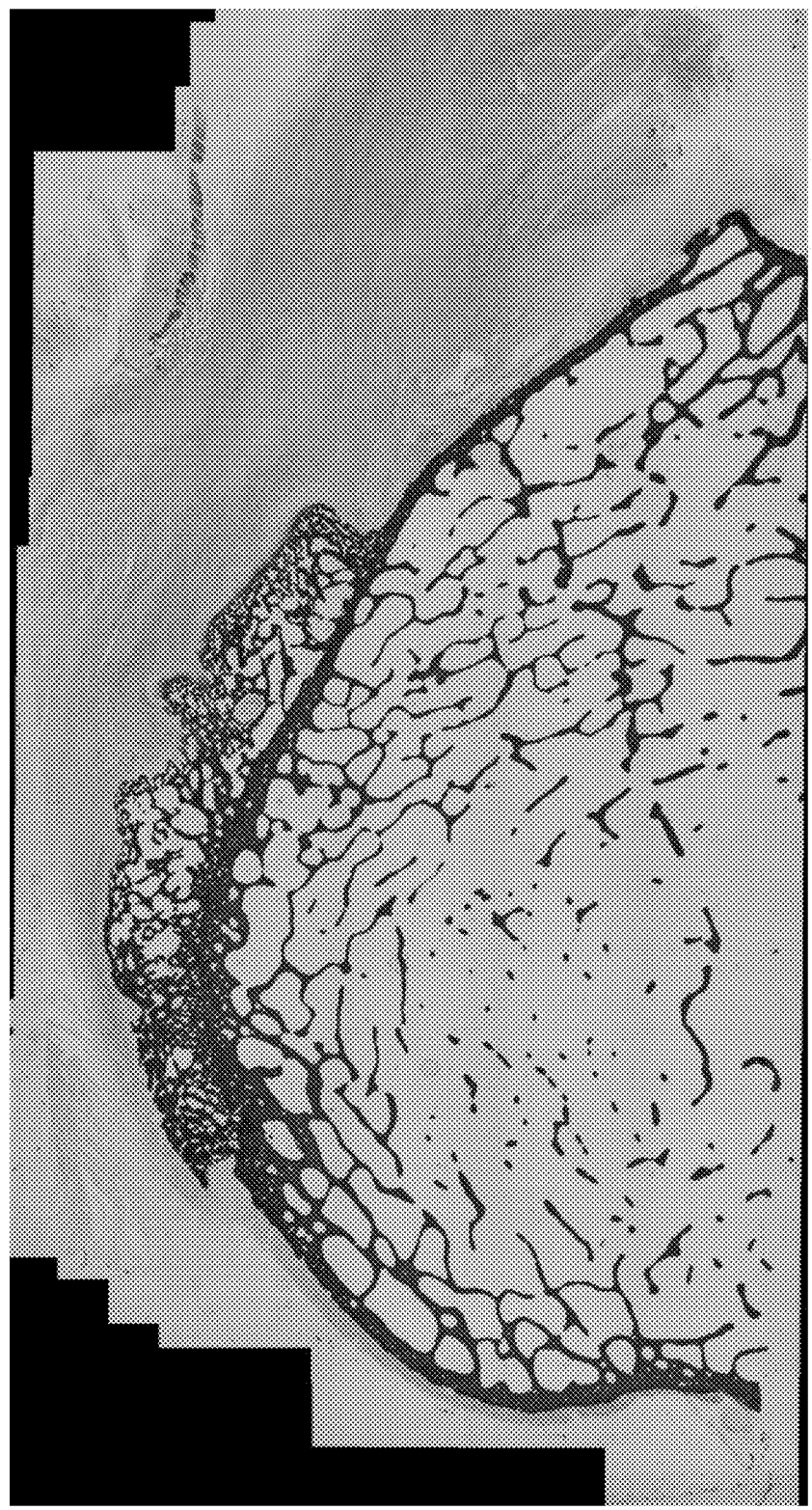
FIG. 4B illustrates a histological sample of an ovine rotator cuff, at 12 weeks, repaired without using a scaffold in accordance with the instant disclosure.
Figure 4C:
FIG. 4C illustrates a histological sample of an ovine rotator cuff, at 12 weeks, repaired with a scaffold in accordance with the instant disclosure.

FIG. 4A illustrates a histological sample of an untreated control rotator cuff (i.e. a contralateral control). FIG. 4B illustrates a histological sample of a treated control rotator cuff at 12 weeks (i.e. a rotator cuff that underwent a repair but did not receive a scaffold as described herein). FIG. 4C illustrates a histological sample of a treated rotator cuff at 12 weeks (i.e. a rotator cuff that underwent a repair and received a scaffold as described herein). This histology illustrates a fibrous scar between the bone and tendon with the suture repair in the samples repaired without a scaffold (e.g. FIG. 4B). Such a scar was not present in the samples repaired with a scaffold as described herein (e.g. FIG. 4C).

FIG. 4B illustrates that, overall at the sub-gross level, the tendon appears similar in thickness to normal or un-manipulated ovine infraspinatus tendon. There is a moderate degree of organization of collagen bundles of the tendon, with some parallel arrangement, however, the organization of collagen is less than that observed in FIG. 4C, with more broad collagen bundles arranged in a haphazard and intersecting manner.

The tendon to bone insertion/enthesis appears more consistent with an "indirect" or Fibrous-type of insertion characterized by diffuse dense tendon-like fibrous tissue immediately attaching along the entire surface of the bone/humeral head. There is no real attempt at re-establishment of a direct/fibrocartilaginous enthesis, with only small focal and extremely thin layers of fibrocartilage (calcified and un-calcified) attaching the tendon to the bone. This cartilage accounts for <5% of surface area between the tendon and bone. Minimal to no inflammation or fibrovascular/granulation tissue is observed.

In FIG. 4C, overall, at the sub-gross level, the tendon appears similar in thickness and organization to normal or un-manipulated ovine infraspinatus tendon. Generally, collagen bundles of the tendon are predominately arranged in more tightly packed parallel bundles.

The insertion of the fibrous tendon with the humeral footprint is beginning to be organized in a manner similar to the "native" direct/fibrocartilaginous insertion of the ovine infraspinatus tendon. Diffusely spanning the majority of the surface area (~75%) of the humeral head/footprint, there is transition from the dense fibrous connective tissue of the tendon to first, a very thin layer of uncalcified fibrocartilage, and then to a more broad/thick layer of calcified fibrocartilage immediately adjacent to the surface of the bone. This organization of the tendon attachment is reminiscent of the direct/fibrocartilaginous type of enthesis native to the ovine infraspinatous tendon with the following exceptions: 1) the attachment and transition of the tendon to fibrocartilage is more diffuse across the entire bone surface of the humeral head as opposed to a more focal attachment typically observed in normal control animals; 2) while an organization of the zones of the enthesis (uncalcified and calcified fibrocartilage) is present and observed, these zones are more thin and less prominent than those observed in a normal control animal; and 3) the calcified fibrocartilage is more similar to hyaline-like cartilage and not uniformly composed linear stacks of chondrocytes arranged perpendicular to the bone. Focally, prominent collagen fibers, similar to "Sharpey" fibers, extend through a region of calcified fibrocartilage and attach to remnant scaffold and the humeral head. Minimal to no inflammation or fibrovascular/granulation tissue was observed.

Figure 5:
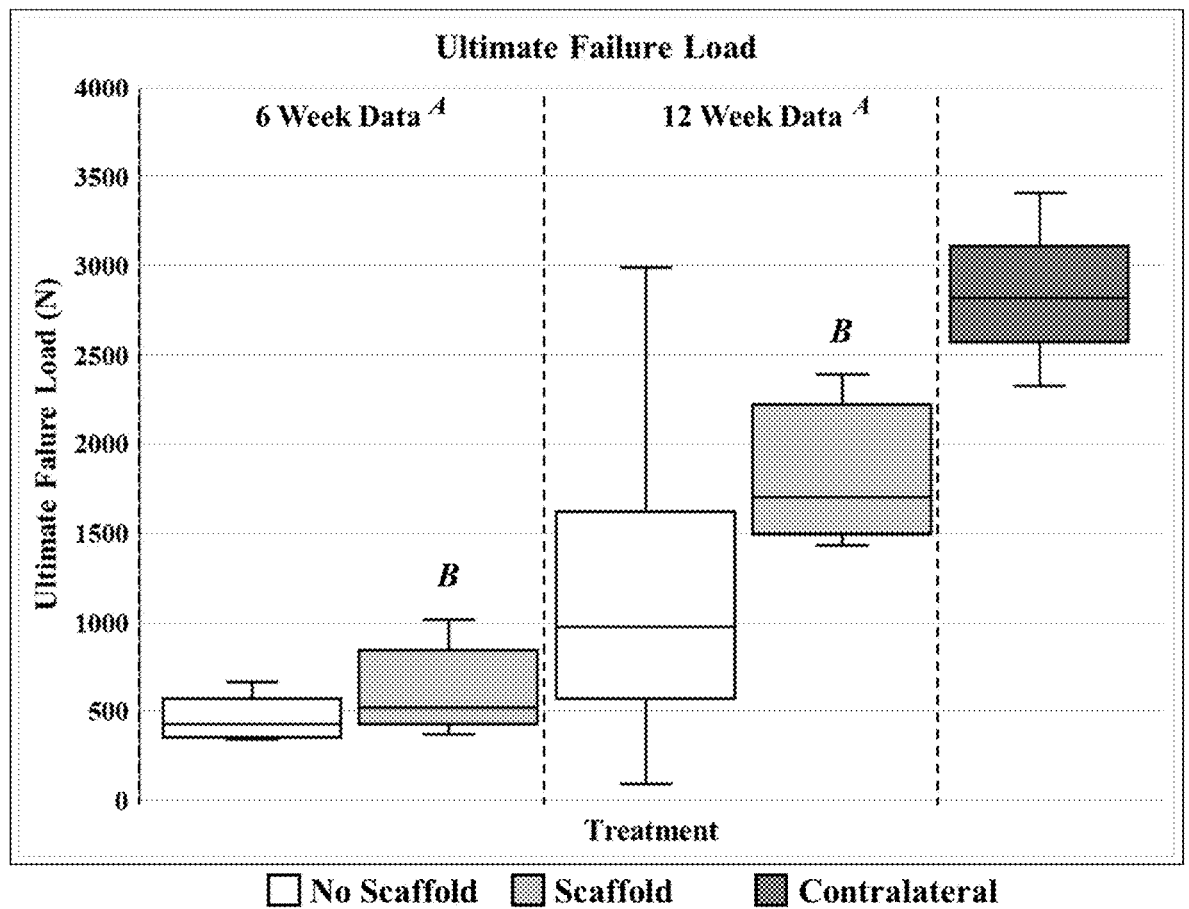
FIG. 5 illustrates ultimate failure load data (N) in 6-week and 12-week samples for each of three experimental groups in an ovine model of rotator cuff repair, in accordance with the instant disclosure. A denotes p=0.003; B denotes p=0.007.

FIG. 5 illustrates ultimate failure load data (N) in the 6-week and 12-week samples for each of the three experimental groups (repair with no scaffold; repair with scaffold; and contralateral control). Comparisons of the means within this set of data had statistical values as shown in Table 1 (note that contralateral samples were not included in the 2-way ANOVA analysis). While the difference in mean values between the experimental groups was not statistically significant, the difference was clinically significant. The lack of statistical significance is due to the large variance in the no-scaffold group at 12 weeks, ranging from 89N to 2,987N within this small population of n=10 per group. The difference in mean values between the no-scaffold and scaffold groups at 12 weeks represents an increase in ultimate failure load of 48%, while the difference in median values between these two groups at 12 weeks represents an increase in ultimate failure load of 74% in the scaffold group. The improved reliability and consistency in the scaffold group, illustrated by the small variance in the scaffold group compared to the no-scaffold group, is a surprising result that underscores the clinical utility of the embodiments described herein.

TABLE 1

| Comparisons for Factor | p-value |
| --- | --- |
| Across time (A) | p = 0.003 |
| Across treatments | p = 0.188 |
| Within 6 weeks | p = 0.682 |
| Within 12 weeks | p = 0.147 |
| Time within "No Scaffold" | p = 0.066 |
| Time within "Scaffold" (B) | p = 0.007 |

Figure 6:
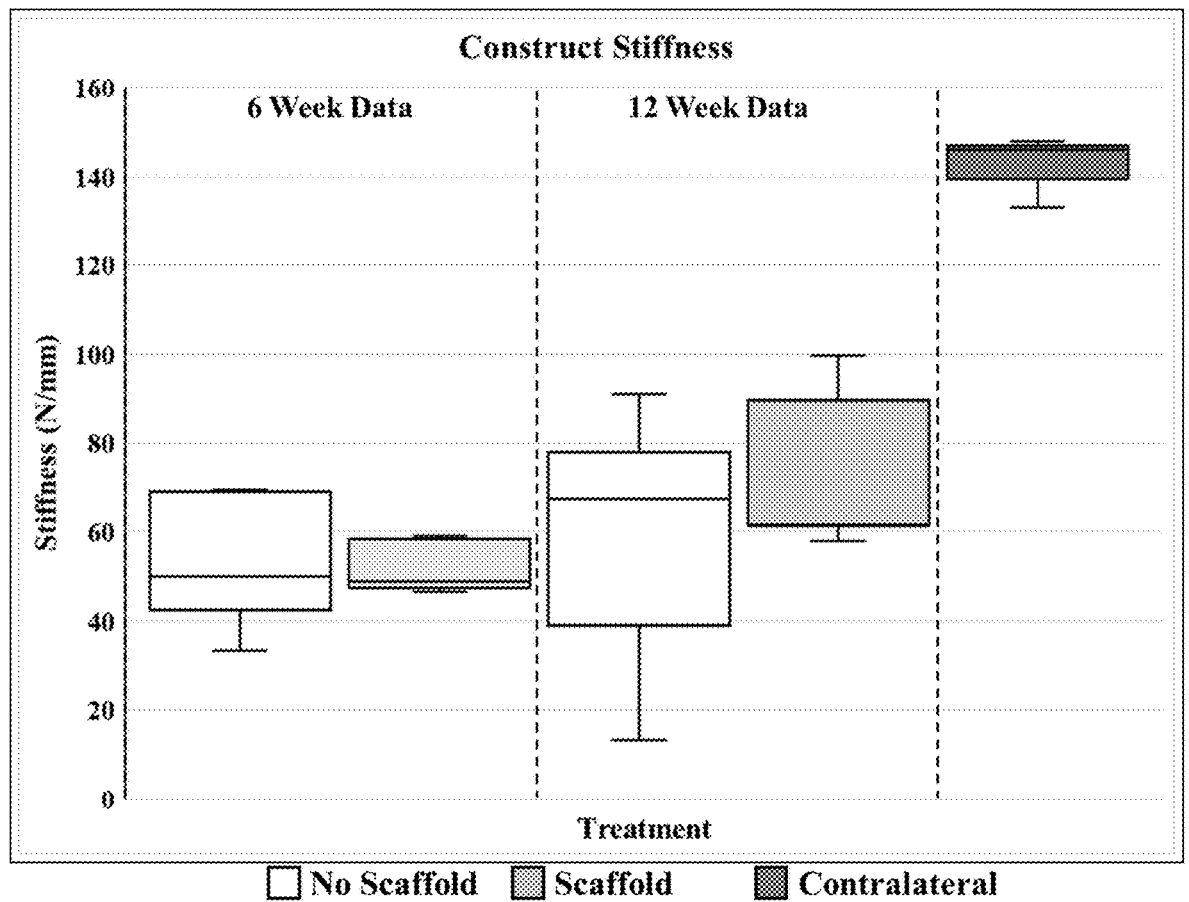
FIG. 6 illustrates construct stiffness data (N/mm) in 6-week and 12-week samples for each of three experimental groups in an ovine model of rotator cuff repair, in accordance with the instant disclosure.

FIG. 6 illustrates construct stiffness data (N/mm) in the 6-week and 12-week samples for each of the three experimental groups (repair with no scaffold; repair with scaffold; and contralateral control). Comparisons within this set of data had statistical values as shown in Table 2 (note that contralateral samples were not included in the 2-way ANOVA analysis). There was no statistically significant interaction between treatment and time (p=0.361).

TABLE 2

| Comparisons for Factor | p-value |
| --- | --- |
| Across time | p = 0.158 |
| Across treatments | p = 0.406 |

Figure 7:
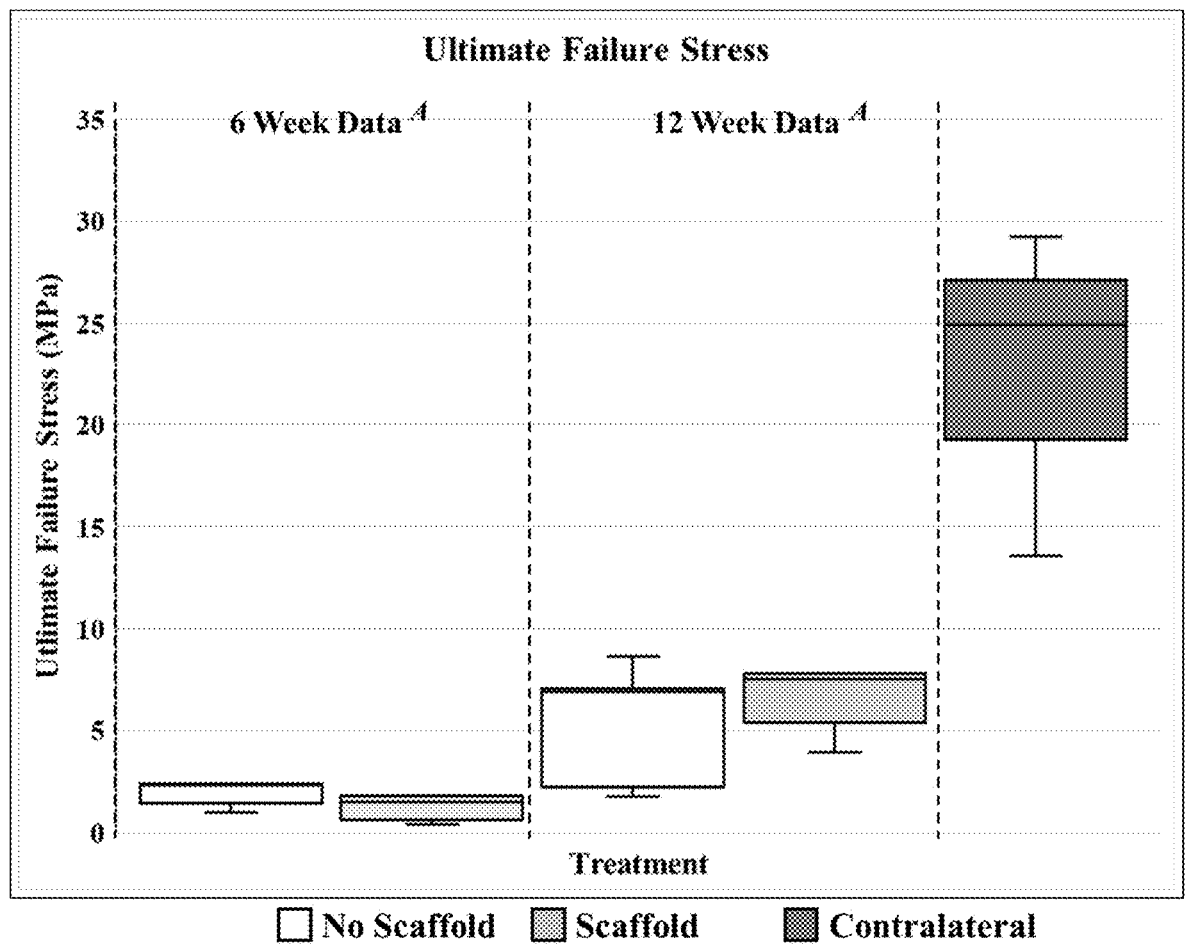
FIG. 7 illustrates ultimate failures stress data (MPa) in 6-week and 12-week samples for each of three experimental groups in an ovine model of rotator cuff repair, in accordance with the instant disclosure. A denotes p<0.001.

FIG. 7 illustrates ultimate failure stress data (MPa) in the 6-week and 12-week samples for each of the three experimental groups (repair with no scaffold; repair with scaffold; and contralateral control). Comparisons within this set of data had statistical values as shown in Table 3 (note that contralateral samples were not included in the 2-way ANOVA analysis). There was no statistically significant interaction between treatment and time (p=0.372).

TABLE 3

| Comparisons for Factor | p-value |
| --- | --- |
| Across time (A) | p < 0.001 |
| Across treatments | p = 0.370 |

Figure 8:
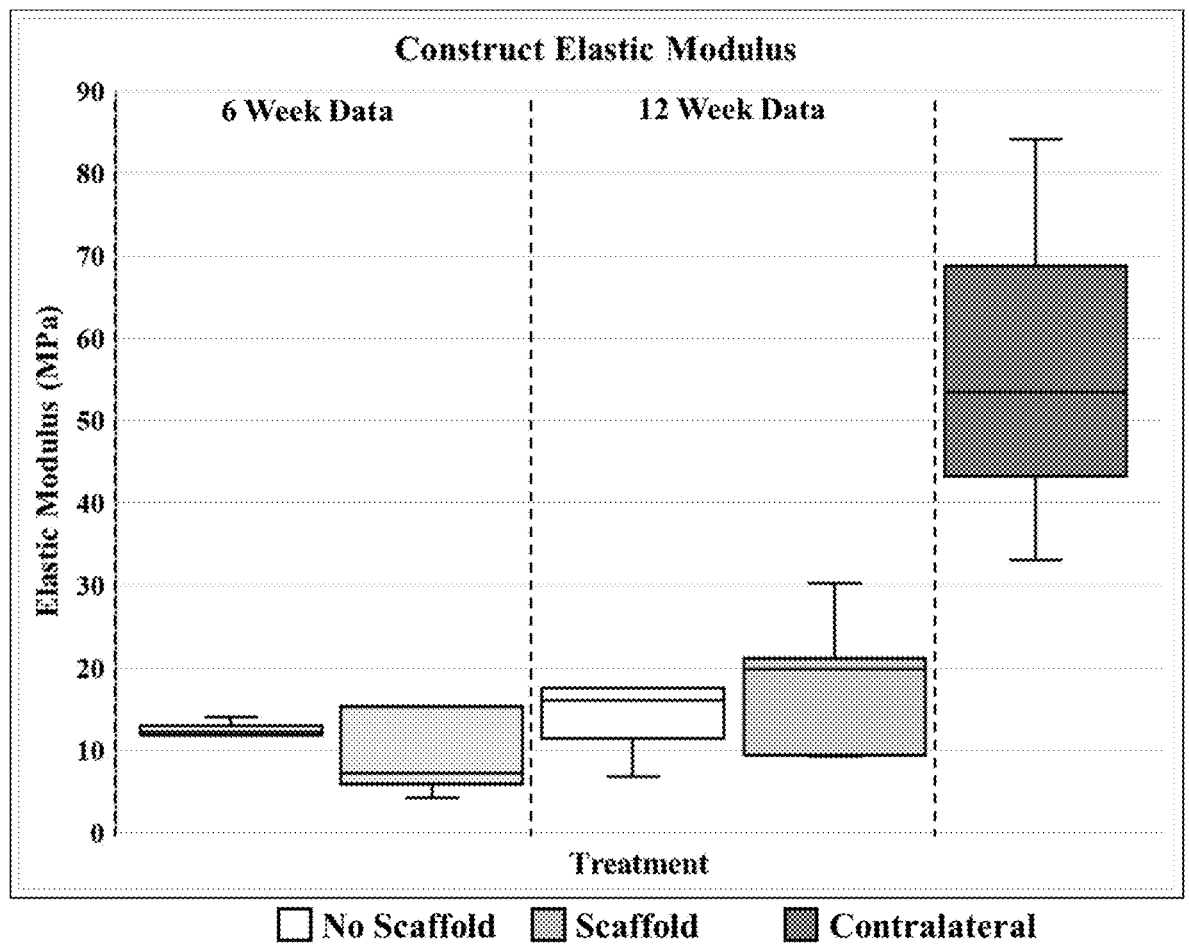
FIG. 8 illustrates construct elastic modulus data (MPa) in 6-week and 12-week samples for each of three experimental groups in an ovine model of rotator cuff repair, in accordance with the instant disclosure.

FIG. 8 illustrates construct elastic modulus data (MPa) in the 6-week and 12-week samples for each of the three experimental groups (repair with no scaffold; repair with scaffold; and contralateral control). Comparisons within this set of data had statistical values as shown in Table 4 (note that contralateral samples were not included in the 2-way ANOVA analysis). There was no statistically significant interaction between treatment and time (p=0.889).

TABLE 4

| Comparisons for Factor | p-value |
| --- | --- |
| Across time | p = 0.175 |
| Across treatments | p = 0.907 |

In summary, the rotator cuffs repaired using a scaffold as described herein demonstrated a 33% increase in breaking strength over the rotator cuffs repaired without such a scaffold at 6 weeks, and a 50% increase at 12 weeks. Histology showed a fibrous scar between the bone and tendon with the suture repair in the samples repaired without a scaffold. Such a scar was not present in the samples repaired with a scaffold as described herein.

While the present disclosure has been illustrated by the description of exemplary embodiments thereof, and while the embodiments have been described in certain detail, it is not the intention of the Applicants to restrict or in any way limit the scope of the appended claims to such detail. Additional advantages and modifications will readily appear to those skilled in the art. Therefore, the disclosure in its broader aspects is not limited to any of the specific details, representative devices and methods, and/or illustrative examples shown and described. Accordingly, departures may be made from such details without departing from the spirit or scope of the Applicant's general inventive concept.

The invention claimed is:

1. A method comprising:
   locating a bone of a subject;
   affixing a tendon or ligament to the bone using a hardware fixture; and
   placing a patch in physical communication with the bone and the tendon or ligament, the patch comprising at least one electro spun polymer fiber;
   wherein the at least one electrospun polymer fiber comprises at least one layer of electrospun polymer fibers that are substantially parallel with respect to one another; and
   wherein the patch is placed such that the substantially parallel electrospun polymer fibers are substantially parallel with the long axis of the tendon or ligament.

2. The method of claim 1, further comprising debriding a portion of the bone of the subject.

3. The method of claim 1, wherein the bone is selected from the group consisting of a humerus, a radius, an ulna, a tibia, a femur, a calcaneus, and combinations thereof.

4. The method of claim 1, wherein the tendon or ligament is selected from the group consisting of a supraspinatus tendon, an infraspinatus tendon, a subscapularis tendon, a deltoid tendon, a biceps tendon, a triceps tendon, an anterior cruciate ligament, a posterior cruciate ligament, a medial collateral ligament, a lateral collateral ligament, an illiotibial band, a quadriceps tendon, a hamstring tendon, a sartorius tendon, an Achilles tendon, a tibialis anterior tendon, and combinations thereof.

5. The method of claim 1, wherein the hardware fixture is selected from the group consisting of a suture anchor in physical communication with a suture, an interference screw, an anchor, and combinations thereof.

6. The method of claim 1, wherein the hardware fixture comprises a suture anchor in physical communication with a suture, and wherein the suture extends through an opening in the patch.

7. The method of claim 1, wherein the at least one electrospun polymer fiber has a diameter of about 0.25 μm to about 20 μm.

8. The method of claim 1, wherein the patch has a length of about 1 mm to about 100 mm, a width of about 1 mm to about 100 mm, and a thickness of about 100 μm to about 5,000 μm.

9. The method of claim 1, wherein the patch further comprises a material selected from the group consisting of tricalcium phosphate, hydroxyapatite, bioglass, and combinations thereof.

10. The method of claim 1, wherein the patch further comprises a biologic component selected from the group consisting of mesenchymal stem cells, tenocytes, fibroblasts, osteoblasts, platelet-rich plasma, bone marrow aspirate, stromal vascular fraction, bursa cells, amnion, growth factors, and combinations thereof.

11. The method of claim 1, wherein the at least one electrospun polymer fiber comprises a polymer selected from the group consisting of polyethylene terephthalate, polyurethane, polyethylene, polyethylene oxide, polyester, polymethylmethacrylate, polyacrylonitrile, silicone, polycarbonate, polyether ketone ketone, polyether ether ketone, polyether imide, polyamide, polystyrene, polyether sulfone, polysulfone, polyvinyl acetate, polytetrafluoroethylene, polyvinylidene fluoride, polycaprolactone, polylactic acid, polyglycolic acid, polylactide-co-glycolide, polylactide-co-caprolactone, polyglycerol sebacate, polydioxanone, polyhydroxybutyrate, poly-4-hydroxybutyrate, trimethylene carbonate, polydiols, polyesters, collagen, gelatin, fibrin, fibronectin, albumin, hyaluronic acid, elastin, chitosan, alginate, silk, copolymers thereof, and combinations thereof.

12. The method of claim 1, wherein the at least one electrospun fiber comprises a first fiber comprising polylactide-co-caprolactone and a second fiber comprising polyglycolic acid, and wherein the first fiber and the second fiber are co-spun.

13. The method of claim 1, wherein the at least one electrospun fiber comprises a co-spun combination of about 50 wt % of fibers comprising polylactide-co-caprolactone fibers and about 50 wt % of fibers comprising polyglycolic acid.

14. A method comprising:
locating a humerus of a subject;
affixing a supraspinatus tendon to the humerus using a suture anchor in physical communication with a suture; and
placing a patch comprising at least one electrospun polymer fiber in physical communication with the humerus and the supraspinatus tendon, such that the patch is between the humerus and the supraspinatus tendon and the suture extends through an opening in the patch;
wherein the at least one electrospun polymer fiber comprises at least one layer of electrospun polymer fibers that are substantially parallel with respect to one another; and
wherein the patch is placed such that the substantially parallel electrospun polymer fibers are substantially parallel with the long axis of the supraspinatus tendon.

15. The method of claim 14, further comprising debriding a portion of the humerus of the subject.

16. The method of claim 14, wherein the at least one electrospun fiber comprises a first fiber comprising polylactide-co-caprolactone and a second fiber comprising polyglycolic acid, and wherein the first fiber and the second fiber are co-spun.

* * * * *